(12) United States Patent
Paulos et al.

(10) Patent No.: US 9,179,976 B2
(45) Date of Patent: Nov. 10, 2015

(54) METHODS OF MAKING COLLAGEN FIBER MEDICAL CONSTRUCTS AND RELATED MEDICAL CONSTRUCTS, INCLUDING TUBES

(75) Inventors: Leon Paulos, Pensacola Beach, FL (US); Mengyan Li, Tampa, FL (US); Daniel Hernandez, Wesley Chapel, FL (US); Thomas J. Koob, Tampa, FL (US)

(73) Assignee: MiMedx Group, Inc., Marietta, GA (US)

( * ) Notice: Subject to any disclaimer, the term of this patent is extended or adjusted under 35 U.S.C. 154(b) by 478 days.

(21) Appl. No.: 13/153,665

(22) Filed: Jun. 6, 2011

(65) Prior Publication Data

US 2011/0282448 A1 Nov. 17, 2011

Related U.S. Application Data

(63) Continuation-in-part of application No. 12/576,435, filed on Oct. 9, 2009, now Pat. No. 9,078,775.

(60) Provisional application No. 61/103,995, filed on Oct. 9, 2008, provisional application No. 61/138,165, filed on Dec. 17, 2008, provisional application No. 61/352,213, filed on Jun. 7, 2010, provisional application No. 61/422,363, filed on Dec. 13, 2010.

(51) Int. Cl.

| | |
|---|---|
| *A61F 2/08* | (2006.01) |
| *B29C 53/58* | (2006.01) |
| *B32B 5/02* | (2006.01) |
| *D02G 3/36* | (2006.01) |
| *D03D 15/00* | (2006.01) |
| *B05D 3/00* | (2006.01) |
| *D02G 3/22* | (2006.01) |
| *A61B 19/02* | (2006.01) |
| *A61L 15/32* | (2006.01) |
| *A61L 27/14* | (2006.01) |
| *A61L 27/24* | (2006.01) |
| *A61L 27/46* | (2006.01) |
| *A61L 27/54* | (2006.01) |
| *A61L 27/58* | (2006.01) |
| *A61B 17/00* | (2006.01) |
| *A61B 17/04* | (2006.01) |
| *A61B 17/06* | (2006.01) |
| *A61B 17/11* | (2006.01) |
| *B29C 53/66* | (2006.01) |

(52) U.S. Cl.

CPC ............ *A61B 19/026* (2013.01); *A61L 15/325* (2013.01); *A61L 27/14* (2013.01); *A61L 27/24* (2013.01); *A61L 27/46* (2013.01); *A61L 27/54* (2013.01); *A61L 27/58* (2013.01); *A61B 17/00491* (2013.01); *A61B 17/0401* (2013.01); *A61B 17/06166* (2013.01); *A61B 17/1128* (2013.01); *A61B 17/1146* (2013.01); *A61B 2017/00526* (2013.01); *A61B 2017/0608* (2013.01); *A61B 2017/06052* (2013.01); *A61B 2017/06071* (2013.01); *A61B 2019/0267* (2013.01); *A61F 2/08* (2013.01); *B29C 53/58* (2013.01); *B29C 53/66* (2013.01); *Y10T 428/249921* (2015.04); *Y10T 428/2938* (2015.01); *Y10T 442/3065* (2015.04)

(58) Field of Classification Search
None
See application file for complete search history.

(56) References Cited

U.S. PATENT DOCUMENTS

| | | |
|---|---|---|
| 3,316,699 A | 5/1967 | Mattingly |
| 3,700,489 A | 10/1972 | Borysko |
| 4,590,928 A | 5/1986 | Hunt et al. |
| 4,778,467 A | 10/1988 | Stensaas et al. |
| 4,792,336 A | 12/1988 | Hlavacek et al. |
| 4,841,962 A | 6/1989 | Berg et al. |
| 4,883,486 A | 11/1989 | Kapadia et al. |
| 4,923,380 A | 5/1990 | Huc et al. |
| 4,979,956 A | 12/1990 | Silvestrini |
| 5,028,695 A | 7/1991 | Eckmayer et al. |
| 5,078,744 A | 1/1992 | Chvapil |
| 5,106,949 A | 4/1992 | Kemp et al. |
| 5,162,430 A | 11/1992 | Rhee et al. |
| 5,256,418 A | 10/1993 | Kemp et al. |
| 5,263,984 A | 11/1993 | Li et al. |
| 5,378,469 A | 1/1995 | Kemp et al. |
| 5,569,302 A | 10/1996 | Proto et al. |
| 5,656,605 A | 8/1997 | Hansson et al. |
| 5,713,374 A | 2/1998 | Pachence et al. |
| 5,718,012 A | 2/1998 | Cavallaro |
| 5,718,717 A | 2/1998 | Bonutti |
| 6,090,117 A | 7/2000 | Shimizu |
| 6,224,630 B1 | 5/2001 | Bao et al. |

(Continued)

FOREIGN PATENT DOCUMENTS

| | | |
|---|---|---|
| CA | 2285161 | 4/2001 |
| EP | 1319415 | 6/2003 |

(Continued)

OTHER PUBLICATIONS

International Search Report and Written Opinion for corresponding PCT application No. PCT/US2011/039375, date of mailing Feb. 23, 2012.

(Continued)

*Primary Examiner* — Robert A Wax
*Assistant Examiner* — Randeep Singh
(74) *Attorney, Agent, or Firm* — Myers Bigel Sibley & Sajovec, P.A.

(57) ABSTRACT

The disclosure describes methods of winding collagen fiber to make medical constructs and related collagen fiber tube and patch devices.

36 Claims, 27 Drawing Sheets

(56) References Cited

U.S. PATENT DOCUMENTS

| | | |
|---|---|---|
| 6,277,397 B1 | 8/2001 | Shimizu |
| 6,280,474 B1 | 8/2001 | Cassidy et al. |
| 6,292,697 B1 | 9/2001 | Roberts |
| 6,335,007 B1 | 1/2002 | Shimizu et al. |
| 6,420,625 B1 | 7/2002 | Jones et al. |
| 6,514,286 B1 | 2/2003 | Leatherbury et al. |
| 6,531,147 B2 | 3/2003 | Sawhney et al. |
| 6,565,960 B2 | 5/2003 | Koob et al. |
| 6,589,257 B1 | 7/2003 | Shimizu |
| 6,592,623 B1 | 7/2003 | Bowlin et al. |
| 6,596,296 B1 | 7/2003 | Nelson et al. |
| 6,645,247 B2 | 11/2003 | Ferree |
| 6,692,528 B2 | 2/2004 | Ward et al. |
| 6,713,537 B1 | 3/2004 | Ueda et al. |
| 6,730,124 B2 | 5/2004 | Steiner |
| 6,752,831 B2 | 6/2004 | Sybert et al. |
| 6,821,530 B2 | 11/2004 | Koob et al. |
| 6,866,681 B2 | 3/2005 | Laboureau et al. |
| 6,936,072 B2 | 8/2005 | Lambrecht et al. |
| 6,953,482 B2 | 10/2005 | Doi et al. |
| 6,955,683 B2 | 10/2005 | Bonutti |
| 6,977,231 B1 | 12/2005 | Matsuda |
| 7,048,963 B2 | 5/2006 | Braithwaite et al. |
| 7,084,082 B1 | 8/2006 | Shimizu |
| 7,090,690 B2 | 8/2006 | Foerster et al. |
| 7,105,021 B2 | 9/2006 | Edens et al. |
| 7,115,146 B2 | 10/2006 | Boyer et al. |
| 7,135,040 B2 | 11/2006 | Wang et al. |
| 7,264,859 B2 | 9/2007 | Rouns et al. |
| 7,309,359 B2 | 12/2007 | Trieu et al. |
| 7,354,627 B2 | 4/2008 | Pedrozo et al. |
| 7,650,742 B2 | 1/2010 | Ushijima |
| 2001/0018619 A1 | 8/2001 | Enzerink et al. |
| 2002/0037940 A1 | 3/2002 | Koob et al. |
| 2002/0123805 A1 | 9/2002 | Murray et al. |
| 2003/0003157 A1 | 1/2003 | Ohan et al. |
| 2003/0100108 A1 | 5/2003 | Altman et al. |
| 2003/0211130 A1 | 11/2003 | Sanders et al. |
| 2003/0230316 A1 | 12/2003 | Glucksman et al. |
| 2004/0110439 A1 | 6/2004 | Chaikof et al. |
| 2004/0131562 A1 | 7/2004 | Gower et al. |
| 2004/0193241 A1 | 9/2004 | Stinson |
| 2004/0224406 A1 | 11/2004 | Altman et al. |
| 2004/0267362 A1 | 12/2004 | Hwang et al. |
| 2005/0009178 A1 | 1/2005 | Yost et al. |
| 2006/0095134 A1 | 5/2006 | Trieu et al. |
| 2006/0100647 A1* | 5/2006 | Doi et al. .................. 606/152 |
| 2006/0200250 A1 | 9/2006 | Ku |
| 2006/0257377 A1 | 11/2006 | Atala et al. |
| 2006/0263417 A1 | 11/2006 | Lelkes et al. |
| 2007/0038290 A1 | 2/2007 | Huang et al. |
| 2007/0118217 A1 | 5/2007 | Brulez et al. |
| 2007/0248643 A1 | 10/2007 | Devore et al. |
| 2007/0269481 A1 | 11/2007 | Li et al. |
| 2008/0020012 A1 | 1/2008 | Ju et al. |
| 2008/0038352 A1 | 2/2008 | Simpson et al. |
| 2008/0124371 A1 | 5/2008 | Turos et al. |
| 2008/0161917 A1 | 7/2008 | Koob et al. |
| 2008/0188933 A1 | 8/2008 | Koob et al. |
| 2008/0199506 A1 | 8/2008 | Horres et al. |
| 2008/0200992 A1 | 8/2008 | Koob et al. |
| 2008/0215150 A1 | 9/2008 | Koob et al. |
| 2008/0286332 A1 | 11/2008 | Pacetti |
| 2008/0300683 A1 | 12/2008 | Altman et al. |
| 2009/0216233 A1 | 8/2009 | Wiedrich et al. |
| 2009/0287308 A1 | 11/2009 | Davis et al. |
| 2010/0076462 A1 | 3/2010 | Bakos et al. |
| 2010/0094318 A1 | 4/2010 | Li et al. |
| 2010/0094404 A1 | 4/2010 | Greenhalgh et al. |

FOREIGN PATENT DOCUMENTS

| | | |
|---|---|---|
| EP | 1493404 | 1/2005 |
| WO | WO 82-01647 | 5/1982 |
| WO | WO 96-14095 | 5/1996 |
| WO | WO01/15754 | 3/2001 |
| WO | WO 01-72241 | 10/2001 |
| WO | WO 2008/033505 A1 | 3/2008 |
| WO | WO 2008-041183 | 4/2008 |
| WO | WO 2008/093342 A2 | 8/2008 |

OTHER PUBLICATIONS

Brunelli et al., Slip-knot flexor tendon suture in zone II allowing immediate mobilisation, The Hand, 1983, vol. 15, pp. 352-358.

Greis et al, The influence of tendon length and fit on the strength of the tendon-bone tunnel complex, Am. J. Sports Med., 2001, 29:493-497.

Becker et al., Early active motion following a beveled technique of flexor tendon repair: Report on fifty cases, Journal of Hand Surgery, 1979, vol. 4 No. 5, pp. 454-460.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Koob et al., Biomimetic approaches to tendon repair, Comp. Biochem. Physiol. A Mol. Integr. Phys., 2002, 133: 1171-1192.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2002, 24:1285-1292.

Koob et al., Biocompatibility of NDGA-polymerized collagen fibers. I. Evaluation of cytotoxicity with tendon fibroblasts in vitro, © 2001John Wiley & Sons, Inc.

Koob et al., Biocompatibility of NDGA-polymerized collagen fibers. II. Attachment, proliferation, and migration of tendon fibroblasts in vitro, © 2001John Wiley & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Messina, The double armed suture: Tendon repair with immediate mobilization of the fingers, Journal of Hand Surgery, 1992, 17A:137-142.

Nottage et al., Arthoscopic Knot Tying Techniques, Arthroscopy: The Journal of Arthroscopic & Related Surgery 15(1999): 515-521.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British Volume,1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

Product advertisement, Conair QB3ECS Quick Braid Styling Kit, © 2007 (1 page).

Integra™ NeuraGen™ Nerve Guide, Product Brochure, 4 pages 2005.

Integra™ NeuraGen™ Nerve Guide, Product Webpage, http://www.integra-ls.com/products/?product=198, Date unknown but believed to be prior to the filing date of the present application, 2 pages.

Integra™ NeuraWrap™ Nerve Protector, Product Webpage, http://www.integra-ls.com/products/?product=198, Date unknown but believed to be prior to the filing date of the present application, 2 pages.

Kakisis, J., et al., Artificial blood vessel: The Holy Grail of peripheral vascular surgery, Journal of Vascular Surgery, vol. 41, Issue 2, 2003, pp. 349-354 (abstract only).

Biosingularity, Advances in biological systems, Google Ad, MIT Technology Review, 2006, 1 Page.

* cited by examiner

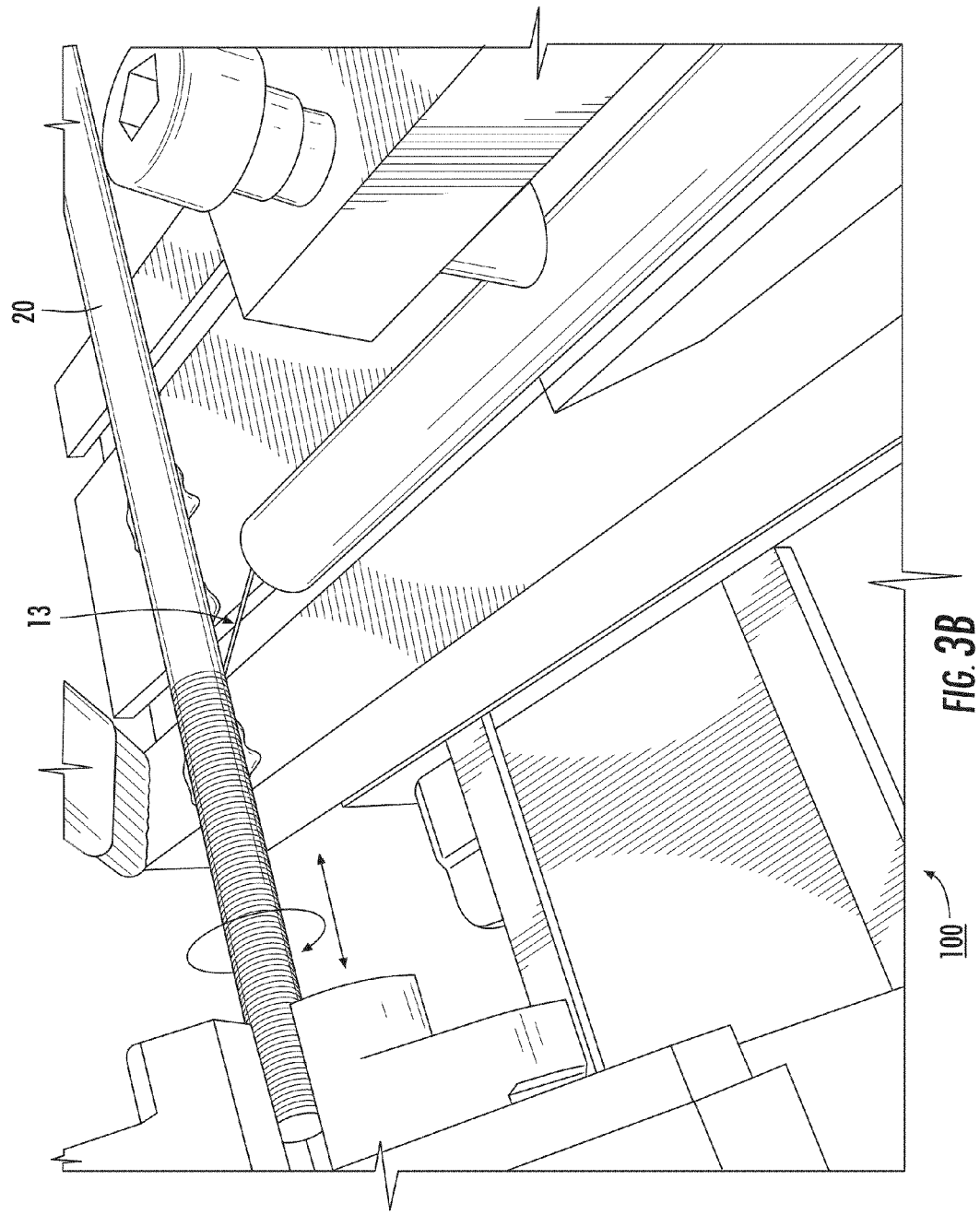

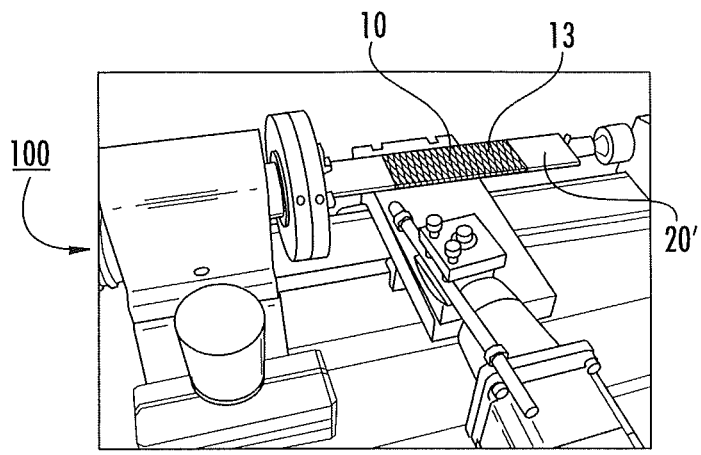
FIG. 3C
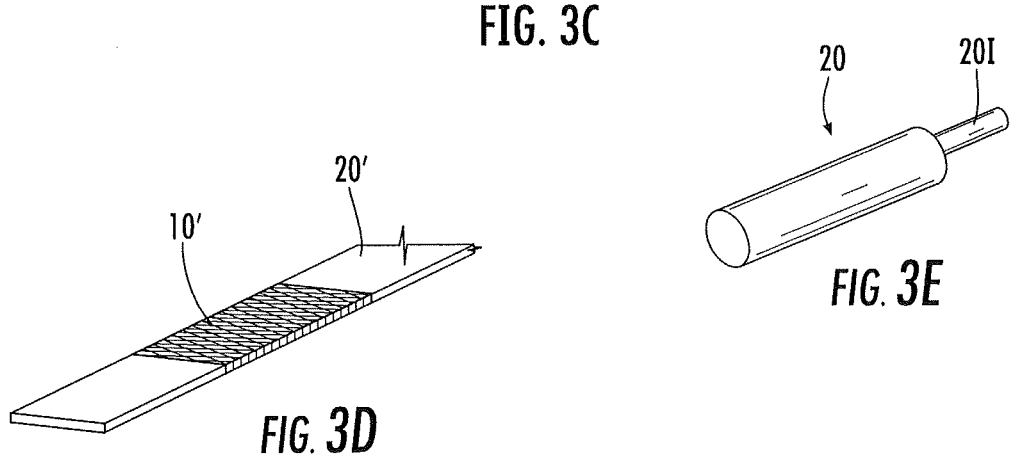
FIG. 3D
FIG. 3E
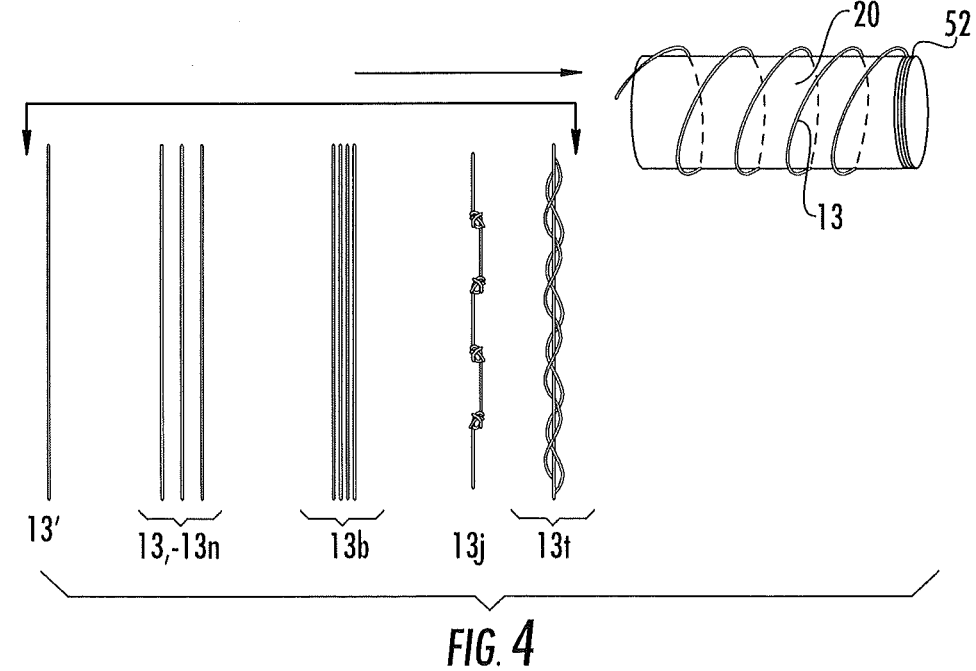
FIG. 4

THE WINDING CAN BE CARRIED OUT SO THAT THE AT LEAST ONE FIBER TURNS ABOUT THE SUPPORT MEMBER IN ONE OF A CLOCKWISE OR COUNTERCLOCKWISE DIRECTION ALONG A FIRST LENGTHWISE DIRECTION FOR A FIRST LAYER, THEN REVERSES TO TRAVEL IN AN OPPOSING LENGTHWISE DIRECTION AND CONTINUES TO TURN ABOUT THE SUPPORT MEMBER IN THE SAME CLOCKWISE OR COUNTERCLOCKWISE DIRECTION TO FORM A SECOND OVERLYING ADJACENT LAYER.
180

FIG. 11

COLLAGEN PAINTING WHILE WINDING FIBERS

GELATIN PAINTING WHILE WINDING FIBERS

COLLAGEN-HA PAINTING WHILE WINDING FIBERS

GELATIN-HA PAINTING WHILE WINDING FIBERS

COLLAGEN/HA

| | THICKNESS MEASUREMENT (mm) | | |
|---|---|---|---|
| | 1ml/tube | 2ml/tube | 3ml/tube |
| | 0.44 | 0.53 | 0.56 |
| | 0.43 | 0.53 | 0.57 |
| | 0.43 | 0.50 | 0.64 |
| | 0.41 | 0.56 | 0.63 |
| | 0.48 | 0.55 | 0.64 |
| | 0.40 | 0.49 | 0.64 |
| | 0.38 | 0.52 | 0.64 |
| | 0.37 | 0.52 | 0.63 |
| | 0.45 | 0.51 | 0.64 |
| | 0.40 | 0.50 | 0.67 |
| MEAN | 0.419 | 0.521 | 0.626 |
| SD | 0.033 | 0.022 | 0.034 |
| THICKNESS: OUTER RADIUS | 0.117 | 0.141 | 0.165 |

10

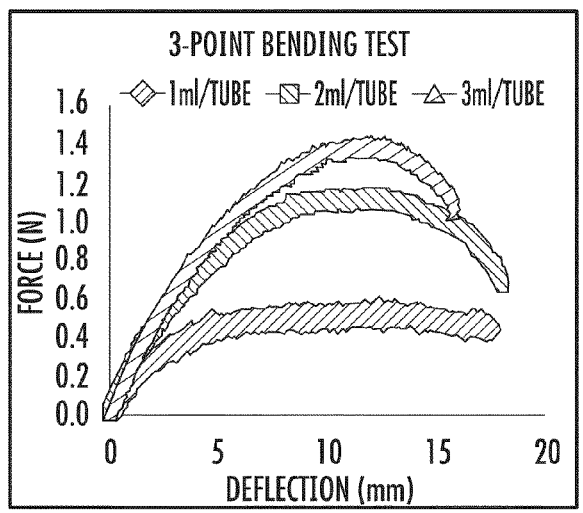
FIG. 18E
| PEAK FORCE (N) | | |
|---|---|---|
| 1ml/TUBE | 2ml/TUBE | 3ml/TUBE |
| 0.54 | 1.14 | 1.41 |
| 0.43 | 1.05 | 1.24 |
| 0.94* | 0.88 | 1.48 |
| 0.52 | 0.97 | 1.33 |
| 0.52 | 0.85 | 1.33 |
| 0.50 | 1.05 | 1.24 |
| MEAN 0.502 | 0.990 | 1.338 |
| SD 0.043 | 0.111 | 0.095 |
FIG. 18F
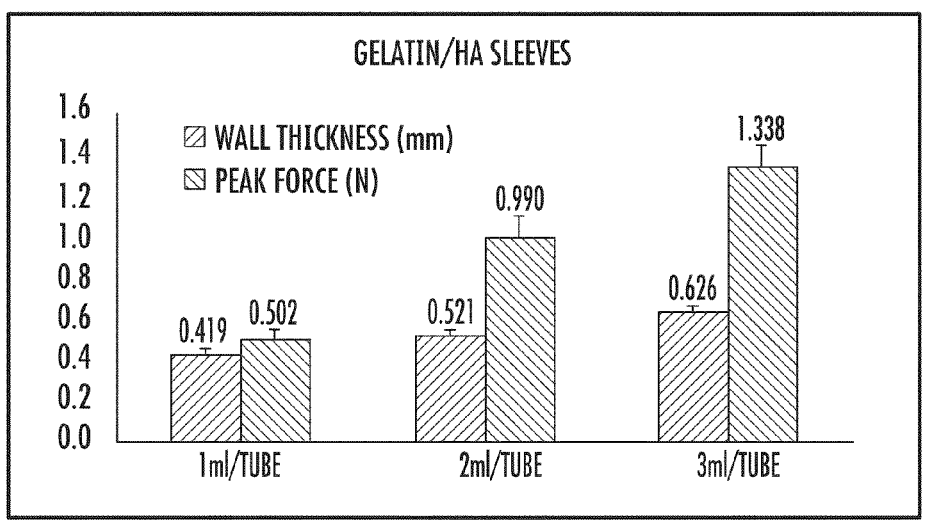
FIG. 18G

METHODS OF MAKING COLLAGEN FIBER MEDICAL CONSTRUCTS AND RELATED MEDICAL CONSTRUCTS, INCLUDING TUBES

RELATED APPLICATIONS

This application is a continuation-in-part application of U.S. patent application Ser. No. 12/576,435 filed Oct. 9, 2009, now U.S. Pat. No. 9,078,775 which claims the benefit of and priority to U.S. Provisional Application Ser. No. 61/103,995 filed Oct. 9, 2008 and U.S. Provisional Application Ser. No. 61/138,165 filed Dec. 17, 2008. This application also claims the benefit of and priority to U.S. Provisional Application 61/352,213, filed Jun. 7, 2010 and U.S. Provisional Application 61/422,363, filed Dec. 13, 2010. The contents of the above documents are hereby incorporated by reference as if recited in full herein.

FIELD OF THE INVENTION

The invention relates to biomedical materials and products.

BACKGROUND OF THE INVENTION

Koob et al. have described methods of producing nordihydroguaiaretic acid (NDGA) polymerized collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs,* Biomaterials 2002 January; 23 (1): 203-12; and U.S. Pat. No. 6,565,960, the contents of which are hereby incorporated by reference as if recited in full herein.

SUMMARY OF EMBODIMENTS OF THE INVENTION

Embodiments of the present invention are directed to methods of making collagen constructs for medical use and related constructs.

Particular embodiments are directed to methods of manufacturing a medical construct. The method can comprise providing at least one collagen fiber at a length of between about 1 m to about 100 m and applying at least one layer of a gelatin slurry onto the at least one collagen fiber to form a construct.

The method can further include winding the at least one collagen fiber a number of revolutions about a length of a support member (e.g. mandrel) having a long axis, the winding having at least one defined pitch and/or fiber angle relative to a long axis of the support member (e.g. mandrel). The support member can be ribbed, smooth, textured, patterned, embossed, and/or rough. The support member can be elongate, planar, flat, tubular, or frustoconical.

The gelatin slurry can comprise one or more minerals and/or particulates. The amount or volume of gelatin slurry applied to the at least one collagen fiber can vary.

The method can include placing a gel of soluble collagen about an outer surface of the support member before the winding step. Multiple layers of collagen gel can be placed on the support member. One or more of the collagen gel layers can comprise one or more minerals. The method can include placing a collagen gel on a ribbed support member and/or the collagen gel can optionally comprise one or more minerals to form a rough inner surface of the construct.

The method can further include placing a gel of soluble collagen over the at least one collagen fiber during and/or after the winding step. Multiple layers of collagen gel can be placed over the at least one collagen fiber. One or more of the collagen gel layers can comprise one or more minerals. The collagen gel can comprise one or more minerals to form a rough outer surface of the construct.

Further embodiments of the present invention are directed to methods of manufacturing a medical construct that include: placing collagen gel about an outer surface of a support member; allowing the collagen gel to dry to form a film on the support member; then winding at least one collagen fiber about the support member over the film; applying a gelatin slurry comprising at least one mineral to a surface of the at least one fiber on the support member; allowing the wound collagen fiber with the gelatin slurry to dry; then applying a collagen gel over the dried collagen fiber with the gelatin slurry; and allowing the applied collagen gel to dry to form an outer layer of film.

Other embodiments of the present invention are directed to medical devices. The medical devices can comprise a tube with a wall surrounding an axially extending cavity. The wall can have at least one wound collagen fiber derived from extruded soluble dermal collagen and a gelatin film attached to the at least one collagen fiber. The gelatin film can include one or more minerals and a gelatin concentration of between about 0.1% to about 40% weight per volume.

Particular embodiments are directed to devices (typically tubes, sleeves or patches) having a wall with at least three layers, including an intermediate layer of at least one collagen fiber arranged in a (repeating) pattern along a length thereof and attached to a gelatin film. The fiber and gelatin film is sandwiched by a collagen film outer surface and a collagen film inner surface. The wall can have one or more integrated minerals. The devices are entirely scalable in all dimensions, length, diameter, wall thickness, relative amount of mineral per collagen, etc. Typically, the devices are tubes that have a length that is between about 5 cm to about 15 cm, a diameter that is between about 3 mm to about 20 mm, and a wall thickness between about 0.1 mm to about 2 mm. The devices can be particularly suitable for allo-grafts or auto-grafts such as tendon or ligament implants.

The devices can be configured as tubes with rough inner and/or outer surfaces. The devices can taper in size about its length or have a substantially constant width (e.g., diameter). The devices can be rough, ribbed, smooth, textured, or patterned. The percent of the at least one mineral in a solution and the constituents of the solution may vary from that described.

Certain embodiments of the invention are directed to a plurality of elongated collagen fibers, wherein the collagen fibers have a length of between about 1 m to about 100 m and are coated at least partially with a gelatin slurry comprising one or more minerals.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 3B is a side perspective view of the device shown in FIG. 3A.

FIG. 3C is a side perspective view of the lathe with a substantially planar elongate support member according to embodiments of the present invention.

FIG. 3D is a side perspective view of a planar support member with a wound collagen fiber(s) according to other embodiments of the present invention.

FIG. 3E is a side perspective view of a tubular support member with an insert according to embodiments of the present invention.

FIG. 4 is a schematic illustration of different collagen fiber configurations that may be used for winding a construct according to embodiments of the present invention.

FIG. 11 is a flow chart of an exemplary winding protocol according to particular embodiments of the present invention.

FIG. 18E is a graph of deflection (mm) v. force (N) from a 3-point bending test performed on collagen fiber constructs prepared with about 1 mL/tube, about 2 mL/tube, or about 3 mL/tube of gelatin/hydroxyapatite solution according to embodiments of the present invention.

FIG. 18F is a chart of the peak force (N) experienced by the tubes during a 3-point bending test according to embodiments of the present invention. The asterisk indicates a value not included in the mean and standard deviation.

FIG. 18G is a bar graph displaying the average wall thickness (mm) and peak force (N) experienced by collagen fiber constructs prepared with about 1 mL/tube, about 2 mL/tube, or about 3 mL/tube of gelatin/hydroxyapatite solution during a 3-point bending test according to embodiments of the present invention.

DETAILED DESCRIPTION

Figure 1A:
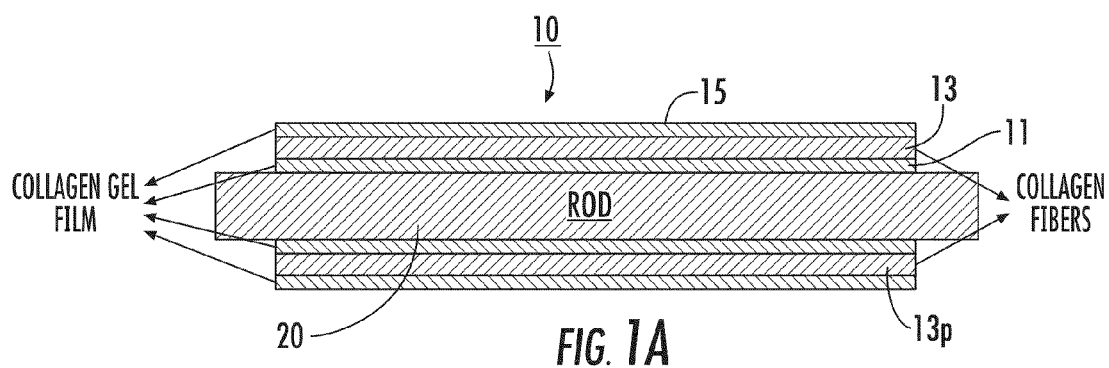
FIG. 1A is a schematic cross-section (in an axial direction) of an exemplary collagen fiber construct on an exemplary support member according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The term "implantable" and derivatives thereof means the device can be inserted, embedded, grafted or otherwise acutely or chronically attached or placed in or on a patient. The term "construct" refers to a device and/or material in a final form for use or in a pre-final form. The term "pitch" means winding or wound at an angle relative to a first plane normal to the longitudinal axis of a core or cavity.

The terms "winding" and "wound" and derivatives thereof means to wrap about an object or center at least once, typically repeatedly, e.g., to turn in a series of circular motions. In some embodiments, at least one collagen fiber (multiple fibers, one or more fiber bundles) turns or rotates its circumferential position about a centerline or long axis. The winding may define a coil (e.g., a series of connected typically substantially concentric rings or spirals), woven and/or braided fiber arrangement with a number of revolutions or turns about a core and/or tube, typically in a regular pattern (but an irregular pattern may also be used) about a length of at least one layer of a tube or cylindrical shape.

Embodiments of the present invention comprise collagen, typically dermal collagen. However, the collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before, where used, oxidizing and polymerizing steps. The collagen can be in the form of microfibrils, fibrils, natural fibers, or synthetic fibers.

In some embodiments, the collagen can be solubilized, dissolved or otherwise transferred into an acid solution, for example, acetic acid (e.g., about 0.01 M to about 1.0 M, typically about 0.5 M), hydrochloric acid (between about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate between about 0.01 M and about 0.5 M, but more typically between about 0.02 M and about 0.1M. The buffer can also be any buffer, including, but not limited to, for example, sodium acetate, 4-(2-hydroxyethyl)-1-piperazineethanesulfonic acid (HEPES), or 3-(N-morpholino)propanesulfonic acid (MOPS). The collagen can be present in a quantity that is at least about 0.1% to about 10%, typically between about 0.1% to about 5% (e.g., about 0.1, 0.2, 0.3, 0.4, 1.0, 2.0, 4.0%) weight per volume, or weight per volume in the neutral buffer solution before fibrillogenesis and fiber formation. In a dried fiber collagen, collagen can be present in an amount of weight by volume of between about 50-100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 nm to about 50 nm in diameter. Fibrils are about 50 nm to about 50 µm in diameter. Natural fibers are above about 50 µm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber.

Of course, synthetic collagen fibers can include non-collagenous components or biocompatible materials, such as particulates, hydroxyapatite and other mineral phases, or drugs that facilitate tissue growth or other desired effects. See, U.S. Pat. No. 6,821,530, incorporated herein by reference above. For example, the fibers and/or constructs formed from same, can include compositions that can contain carbon nano-tubes, zinc nano-wires, nano-crystalline diamond, or other nano-scale particulates; and larger crystalline and non-crystalline particulates such as calcium phosphate, calcium sulfate, apatite minerals. For example, the compositions can also or alternatively contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or fiber-derived constructs can contain cells, engineered cells, stem cells, and the like. Combinations of the above or other materials can be embedded, coated and/or otherwise directly or indirectly attached to the collagen fibers and/or construct formed of same.

The term "collagen gel" means a semi-solid (e.g., gelatinous density) material that includes collagen fiber, fibrils and/or microfibrils, typically dermal collagen, that has been acid or pepsin solubilized (e.g., soluble collagen) and processed to maintain the collagen in its molecular form. The collagen concentration of the soluble collagen and/or resulting soluble collagen gel can be between about 0.1% to about 4% weight per volume. The collagen can be solublized, dissolved, and/or suspended in a solution (e.g., water or buffer solution). The solution can be a neutralized solution with a pH of about pH 7.0 to about 7.4. The pH can be about 7.0, 7.1, 7.2, 7.3, or 7.4. In some embodiments the pH is about 7.2. The buffer can be any buffer, including, but not limited to, for example, sodium acetate, 4-(2-hydroxyethyl)-1-piperazineethanesulfonic acid (HEPES), or 3-(N-morpholino)propanesulfonic acid (MOPS) at a pH of about pH 7.0 to about 7.4. The soluble collagen gel may be formed to be in a cylindrical shape of a defined length and diameter, typically with a diameter of between about 0.1 cm to about 1 cm, and a length of between about 5 cm to about 100 m, more typically between about 1 m to about 50 m.

The collagen gel can comprise non-collagenous components or biocompatible materials, such as one or more particulates and/or minerals. Exemplary minerals include, but are not limited to, calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and calcium sulfate. One or more minerals can be present in a quantity from about 0.1% to about 5%, typically between about 0.1% to about 1% (e.g., 0.1, 0.2, 0.4, 0.6, 0.8, or 1%) weight per volume. When one or more minerals and/or particulates are present in the collagen gel, the collagen gel can be used to create a rough or textured surface. "Rough" as used herein refers to an unequal or varied surface that can contain surface texture, ridges, and/or bumps. In some embodiments at least one mineral is present in the collagen gel to create a rough inner and/or outer surface. The higher the mineral concentration in the collagen gel, typically, the rougher the surface and/or resulting tube. A high mineral concentration can provide a surface and/or a tube that is lighter in color than a surface and/or tube containing no minerals.

The collagen fibers and collagen gel can be produced in batch or continuous-type systems, including wet gel collagen extrusion systems, which produce cylindrical lengths of gel that can be allowed to substantially dry (actively or passively) to obtain a suitable length of fiber. Examples of some collagen fiber production processes that can generate soluble collagen in suitable lengths are described in U.S. Pat. No. 6,565,960, and pending U.S. Patent Application Publication No. US-2008-0188933-A1, the contents of which are hereby incorporated by reference.

The collagen fibers can be spooled for supplying to an automated or semi-automated winder to form the biomedical construct. The collagen fibers may be formed with a relatively thin diameter, such as, for example between about 0.05 mm to about 0.2 mm (average), such as about 0.08 mm dry diameter (average) and about a 0.13 mm wet diameter (average).

The term "gelatin" refers to denatured collagen. Gelatin can be derived from collagen in a well known manner or can be obtained from commercial suppliers, such as Sigma-Aldrich®, located in St. Louis, Mo. An exemplary method of obtaining gelatin is by heating collagen at a suitable temperature to cause it to become denatured. Denaturation results in the irreversible transformation of collagen into a random coiled structure, which is gelatin. Gelatin can be derived from one or more sources of collagen and derived from one or more types of collagen, such as but not limited to, types I, II, III, and/or VI. Exemplary sources from which gelatin is derived include, but are not limited to, sea cucumber dermis collagen, bovine, caprine, porcine, ovine or other suitable donor mammal collagen, and marine animal collagen such as chinoderms. The gelatin can be derived from collagen obtained from mammalian cells synthesized in vitro. The gelatin can be derived from collagen obtained from molecularly engineered constructs and synthesized by bacterial, yeast or any other molecularly manipulated cell type.

The term "gelatin slurry" as used herein refers to a mixture of gelatin in a solvent (e.g., water or buffer solution). The gelatin slurry can be a homogeneous or heterogeneous mixture. Gelatin in the gelatin slurry can be suspended, solubilized, and/or dissolved (e.g., completely or partially) in a solvent to form a gelatin slurry. The gelatin slurry can comprise other components, such as, but not limited to, one or more minerals and/or particulates, that can be suspended, solubilized, and/or dissolved in the solvent. The buffer can be any buffer, including, but not limited to, for example, sodium acetate, 4-(2-hydroxyethyl)-1-piperazineethanesulfonic acid (HEPES), or 3-(N-morpholino)propanesulfonic acid (MOPS) at a pH of about pH 6.5 to about 7.8. The pH of the buffer can be about 6.5, 6.6, 6.7, 6.8, 6.9, 7.0, 7.1, 7.2, 7.3, 7.5, 7.4, 7.6 or 7.8. In some embodiments the pH is about 7.2. The gelatin can also or alternatively be dissolved in a neutral buffered solution either with or without salts, e.g., phosphate buffer at about pH 6.5 to about 7.8, or phosphate buffered saline at about pH 6.5 to about 7.8. The phosphate buffer can be at any concentration of sodium phosphate between about 0.01 M and about 0.5 M, but more typically between about 0.02 M and about 0.1 M. The gelatin can be present in a quantity from about 0.1% to about 60%, typically between about 2% to about 40% (e.g., about 2, 3, 4, 5, 6, 7, 8, 10, 15, 20, 25, 30, 35, or 40%) weight per volume.

The gelatin slurry can be heated to create a viscous slurry at a temperature that keeps the gelatin from gelling or solidifying during application, and/or to dissolve or solubilize the gelatin in the solvent. When a gelatin slurry is cooled to a sufficient temperature a "gelatin hydrogel" is formed. The term "gelatin hydrogel" as used herein refers to a semi-solid (e.g., gelatinous density) material formed by the gelatin slurry that includes gelatin and can comprise other components, such as, but not limited to, one or more minerals and/or particulates. The gelatin in the gelatin slurry and in the resulting gelatin hydrogel are composed of denatured collagen and cannot be used to produce collagen fibers, fibrils, and/or microfibrils. To be clear, in contrast, the term "collagen gel" as used herein refers to a gel that includes collagen fiber, fibrils and/or microfibrils that has been acid or pepsin solubilized (e.g., soluble collagen) and processed to maintain the collagen in its molecular form, whereas the terms "gelatin hydrogel" and "gelatin slurry" as used herein refer to compositions of gelatin, which is denatured collagen that cannot be used to produce collagen fibers, fibrils, and/or microfibrils. Stated differently, gelatin is denatured collagen which does not maintain collagen in its molecular form since it is irreversibly transformed into a random coiled structure.

The gelatin slurry and/or the gelatin hydrogel, which may or may not be attached to at least one collagen fiber, can be cross-linked with a suitable polymerizing (i.e., cross-linking) material, such as, but not limited to, NDGA, carbodiimide, glutaraldehyde, formaldehyde, tannic acid, isocyanates, and epoxy resins, or may be used in a non-cross-linked state. Alternatively or in addition, the gelatin slurry and/or gelatin hydrogel can be stabilized with treatments, such as, but not limited to, one or more of dehydrothermal treatment, glycation, and ultraviolet light. The gelatin slurry and/or the gelatin hydrogel treated with a polymerizing material and/or a stabilization treatment can be resistant to liquification at 37° C. and/or thermally stable at temperatures over about 37° C. The gelatin slurry and/or the gelatin hydrogel treated with a polymerizing material and/or a stabilization treatment can be thermally stable at temperatures up to about 120° C., typically at temperatures between about 37° C. to about 104° C. The polymerized and/or stabilized gelatin hydrogel can be stronger and/or stiffer than an untreated gelatin slurry and/or gelatin hydrogel (e.g., an untreated gelatin hydrogel has a compressive stiffness of about 0.70 MPa, compared to about 4.71 MPa for NDGA-treated gelatin hydrogel). The polymerized and/or stabilized gelatin hydrogel can be nearly elastic under dynamic compression loads (e.g., rebounds substantially completely after compression to over 80%, while untreated gelatin hydrogels fracture when compressed to 80%). The polymerized and/or stabilized gelatin hydrogel can undergo large deformations without comprising its mechanical properties. According to some embodiments, the gelatin slurry and/or the gelatin hydrogel, if polymerized (i.e., cross-linked) and/or stabilized, can be polymerized and/or stabilized at any time either before, during, and/or after application and/or drying to at least one collagen fiber, where applied.

One or more minerals can be added to the gelatin slurry. The mineral can support bone ingrowth and/or osteointegration. In some embodiments the mineral can integrate into bone structures and support bone growth without breaking down or dissolving. Exemplary minerals include, but are not limited to, calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and calcium sulfate. The one or more minerals can be present in a quantity from about 0.1% to about 50% weight per volume, typically between about 0.1% to about 30% (e.g., 0.1, 0.2, 0.5, 0.7, 1, 2, 3, 4, 5, 6, 8, 10, 12, 15, 20, 25, or 30%) weight per volume. When one or more minerals and/or particulates are present in the gelatin slurry, the resulting gelatin hydrogel can have suspended particulates that are visually detectable with and/or without the use of a scanning electron microscope (SEM) and/or the resulting surface of a tube can be rough. For example, a higher mineral concentration in the gelatin slurry can provide a rougher resulting tube and/or a tube that is lighter in color. The mineral, in some particular embodiments, is hydroxyapatite. Exemplary gelatin slurries are provided in Tables 1 and 2 below.

TABLE 1

Exemplary gelatin slurries.
Component Concentration (wt/vol)

| Mineral (e.g., Hydroxyapatite) | Gelatin |
|---|---|
| 0.5% | 3% |
| 1% | 20% |
| 2% | 2% |
| 2.5% | 15% |
| 3% | 35% |
| 5% | 10% |
| 5% | 1.5% |
| 8% | 40% |
| 10% | 2% |
| 10% | 10% |
| 12% | 0.5% |
| 15% | 2.5% |
| 15% | 25% |
| 20% | 1% |
| 20% | 3% |
| 20% | 25% |
| 23% | 3.5% |
| 25% | 25% |
| 25% | 35% |
| 30% | 2% |
| 30% | 5% |
| 30% | 40% |

TABLE 2

Exemplary gelatin slurries comprising a combination of minerals.
Component Concentration (wt/vol)

| Gelatin | Hydroxyapatite | Calcium Sulfate | Tricalcium Phosphate |
|---|---|---|---|
| 0.5% | 7.5% | 7.5% | |
| 1% | 2% | 2% | 2% |
| 1% | | 12% | 12% |
| 1.5% | 5% | | 5% |
| 2% | 7.5% | | 2.5% |
| 2% | 10% | 10% | 10% |
| 3% | 2% | 10% | 5% |
| 5% | | 1.5% | 2% |
| 5% | 7.5% | 12.5% | |
| 10% | 2.5% | 2.5% | 2.5% |
| 10% | 15% | 5% | |
| 15% | | 7.5% | 7.5% |
| 20% | 2.5% | 10.5% | |
| 20% | 10% | | 15% |
| 25% | 3.5% | 7.5% | |
| 30% | 3.5% | 1.5% | 0.5% |
| 30% | 15% | 15% | |
| 35% | 15% | 10% | 5% |
| 35% | 6% | | 9% |
| 40% | | 5% | 2.5% |

The gelatin slurry can be heated prior to application typically above room temperature, such as up to about 120° C. or even more. In some embodiments, the gelatin slurry can be heated and/or kept at between about room temperature and about 100° C., typically between about room temperature and about 70° C. to keep the gelatin from gelling or solidifying during application, and/or to dissolve or solubilize the gelatin and/or one or more minerals in the solvent.

During application of the gelatin slurry onto a construct (e.g., collagen fiber), the gelatin slurry can be heated above room temperature, such as between about 20° C. and about 70° C., between about 20° C. and about 60° C., typically between about 45° C. to about 55° C. to keep the gelatin from gelling or solidifying during application, and/or to dissolve or solubilize the gelatin and/or one or more minerals in the solvent.

The gelatin slurry can be heated by known methods and devices, such as, but not limited to, heating using a water bath, heating block, heating pad, solar or light source, microwave, or bunsen burner. The temperature to which the gelatin slurry is heated can depend on the concentration of gelatin and/or other components present in the slurry. Typically, if a high concentration of gelatin and/or other components is present in the gelatin slurry, then the gelatin slurry may need to be heated to a higher temperature to create a viscous slurry at a temperature that keeps the gelatin from gelling or solidifying during application, and/or to dissolve or solubilize the gelatin and/or other components in the solvent. Generally, the higher the concentration of gelatin in the slurry, the higher the temperature needed to create a viscous slurry at a temperature that keeps the gelatin from gelling or solidifying during application, and/or to dissolve or solubilize the gelatin in the solvent. However, other components present in the gelatin slurry, e.g., minerals, may affect the viscosity of the gelatin slurry, the temperature at which the gelatin slurry gels or solidifies, and/or the solubility of the gelatin and/or minerals in the solvent. Thus, the temperature to which the gelatin slurry is exposed or heated to can vary.

The term "film" refers to a thin layer of collagen gel, gelatin slurry (typically comprising one or more minerals), and/or gelatin hydrogel (typically comprising one or more minerals) that has dried. The collagen gel, gelatin slurry, and/or gelatin hydrogel can be actively and/or passively dried. Exemplary methods of drying the collagen gel, gelatin slurry, and/or gelatin hydrogel include, but are not limited to, air drying, drying under heat, or drying in an oven or dryer using conduction, convection, infrared/radiant, or radio frequency. The moisture content of the resulting collagen film and/or gelatin film can be less than about 25% by weight of the film, less than about 15% by weight of the film, but is typically less than about 5% by weight of the film to provide a state of the collagen film and/or gelatin film at a low moisture content.

Several layers of the collagen gel, gelatin slurry, and/or gelatin hydrogel can be applied or used to generate the desired film thickness or coverage. For example, between about 1-20 layers of collagen gel, gelatin slurry, or gelatin hydrogel can be applied to form a collagen film or gelatin film, typically between about 1-10 layers of collagen gel, gelatin slurry, or gelatin hydrogel can be applied to form a collagen film or gelatin film. As will be discussed further below, in particular embodiments, between about 1-20 layers of collagen gel are placed about an outer surface of a support member (e.g., 20 FIG. 1A, 20' FIG. 3C, 20r FIG. 19A, and 20f FIG. 20A) and allowed to dry, then, at least one collagen fiber is wound a number of revolutions about a length of the support member and while winding the at least one collagen fiber between about 1-20 layers of a gelatin slurry are applied to the at least one collagen fiber and optionally allowed to dry, then, between about 1-20 layers of collagen gel are placed onto the at least one collagen fiber with the gelatin hydrogel or gelatin film and allowed to dry.

The one or more layers of collagen gel, gelatin slurry, and/or gelatin hydrogel can comprise different components and/or comprise the same components present in different concentrations. In certain embodiments, each of the layers comprise the same components, e.g., minerals and particulates, and in other embodiments the layers comprise different components. In particular embodiments, each of the layers comprise the same components, but in each layer the concentration of the components is different. For example, in certain embodiments, the mineral concentration in a first (inner) layer can be less than the mineral concentration in the outer layer. The film can be present in a thickness that is between about 5 microns and about 1 mm, typically between about 5 microns and about 700 microns, and more typically between about 5 microns and about 500 microns. The film of gelatin hydrogel is typically thicker than the film of collagen gel.

The collagen and/or gelatin film can be permeable and flexible and optically transmissive, e.g., translucent or transparent, or may be opaque. The color of the collagen gel, gelatin slurry, and/or gelatin hydrogel can vary depending on the components present in the gel and their concentration. In certain embodiments the greater the mineral concentration present in the collagen gel, gelatin slurry, and/or gelatin hydrogel, the lighter the gel and/or resulting construct (e.g., tube). The color or transmissive characteristics of the collagen film and/or gelatin film can vary within the film. The color or transmissve characteristics of the collagen film and/or gelatin film may change when hydrated. The film can infuse into, migrate and/or bond to a collagen fiber to form a collagen fiber laminate. A "laminate" as used herein refers to the joining of two materials by any manner, such as, but not limited to, by adhesion to one another. The materials can be the same or different. The collagen fiber can be coiled or wound (dry). The film is not required. In some embodiments, a collagen gel, where used, can provide a smooth (and typically a substantially constant diameter) surface over and/or under the at least one collagen fiber. In other embodiments, a collagen gel comprising one or more minerals, e.g., hydroxyapatite, where used, can provide a rough layer (e.g., inner and/or outer surface) over and/or under the at least one collagen fiber.

Figure 15A:
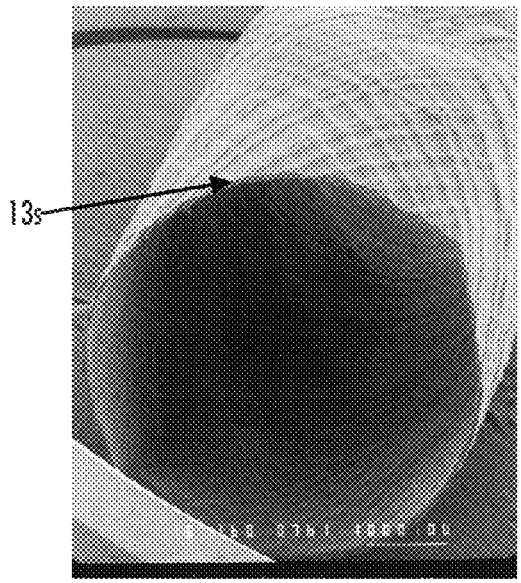
FIG. 15A is a scanning electron microscope image of a cut edge of a collagen fiber construct prepared with collagen painting while winding the at least one collagen fiber according to embodiments of the present invention.
Figure 15B:
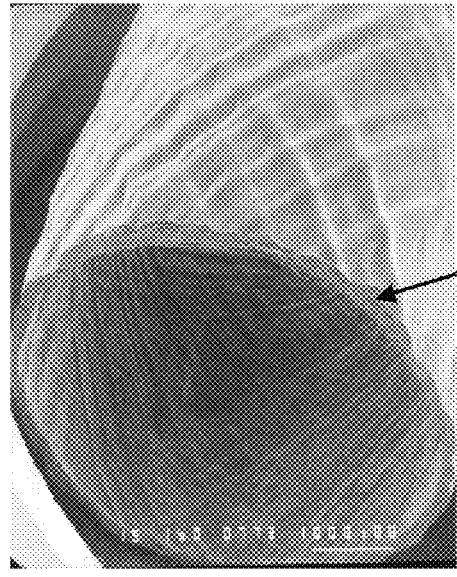
FIG. 15B is a scanning electron microscope image of a cut edge of a collagen fiber construct prepared with gelatin painting while winding the at least one collagen fiber according to embodiments of the present invention.
Figure 15C:
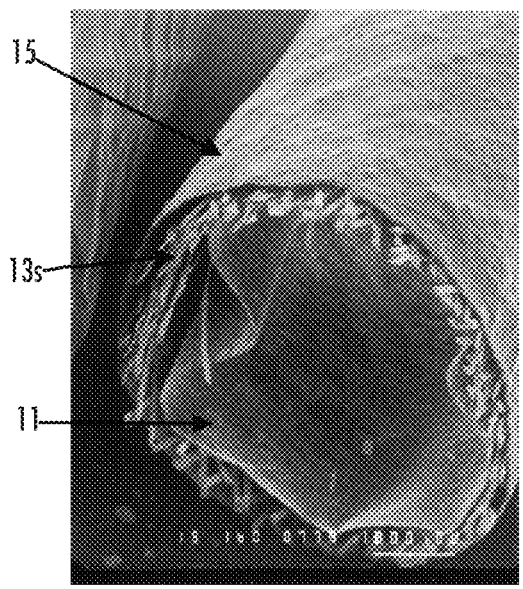
FIG. 15C is a scanning electron microscope image of a cut edge of a collagen fiber construct prepared with collagen/hydroxyapatite painting while winding the at least one collagen fiber according to embodiments of the present invention.
Figure 15D:
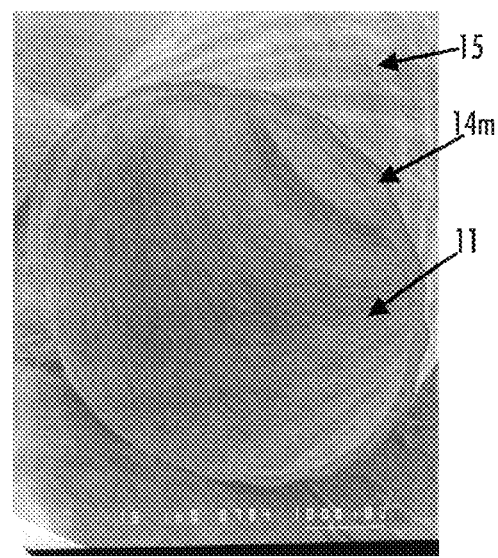
FIG. 15D is a scanning electron microscope image of a cut edge of a collagen fiber construct prepared with gelatin/hydroxyapatite painting while winding the at least one collagen fiber according to embodiments of the present invention.

Referring now to the figures, FIG. 1A, an exemplary elongate construct 10 is shown on a support member 20. As shown, the construct 10 includes an inner layer of collagen film 11, an intermediate layer of at least one wound collagen fiber 13, and an outer layer of collagen film 15. Referring to FIGS. 13F, 15A, and 15C, the intermediate layer 13s can comprise at least one wound collagen fiber and one or more layers of collagen gel and/or collagen film optionally including one or more minerals and/or particulates. Referring to FIG. 15B, for example, the intermediate layer 14 can comprise at least one wound collagen fiber and one or more layers of gelatin slurry, gelatin hydrogel, and/or gelatin film optionally including one or more minerals and/or particulates. An intermediate layer comprising at least one wound collagen fiber and one or more layers of gelatin slurry, gelatin hydrogel, and/or gelatin film comprising one or more minerals 14m is demonstrated in FIG. 15D.

In other embodiments, the construct 10 can be formed without the inner and/or outer layer of film 11 and/or may optionally include other materials or constituents and/or layers. For example, hydroxyapatite can be placed into the collagen fiber and/or collagen gel material. This configuration can be particularly suitable to augment fixation of autograft tendons (typically with one or more interference screws).

Figure 1B:
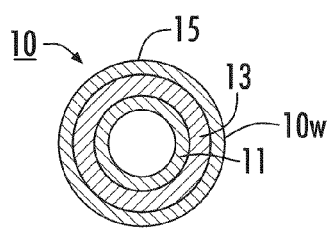
FIG. 1B is an end view of the device shown in FIG. 1A (shown without the support member) according to embodiments of the present invention.
Figure 2B:
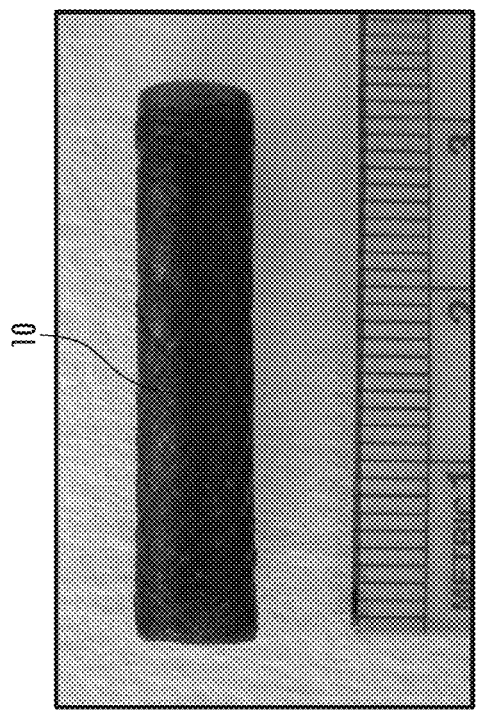
FIGS. 2A-2D are digital photographs of a prototype of a collagen fiber construct that may be particularly suitable for a medical construct, such as a nerve guide, according to embodiments of the present invention.
Figure 2D:
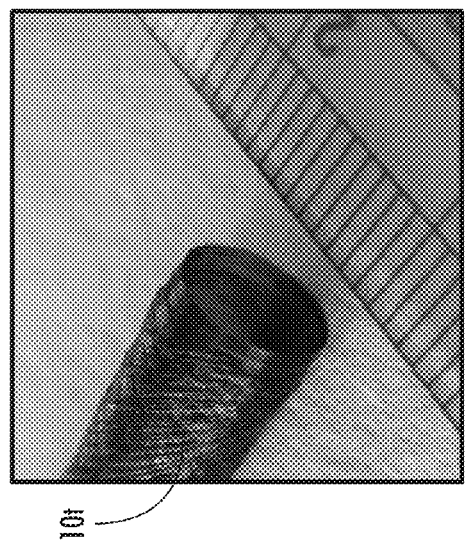
Figure 2A:
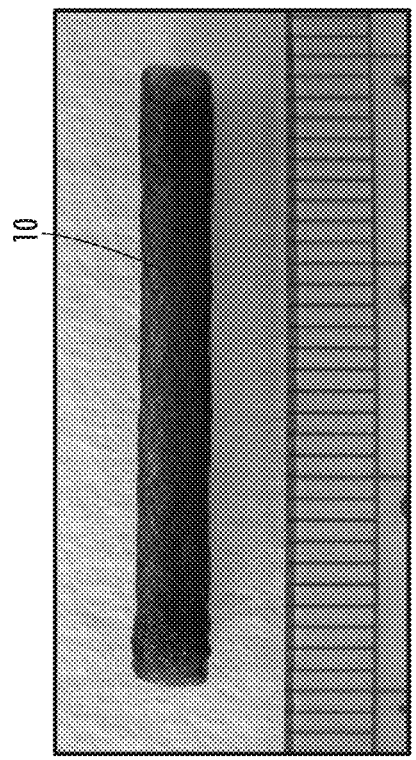
Figure 2C:
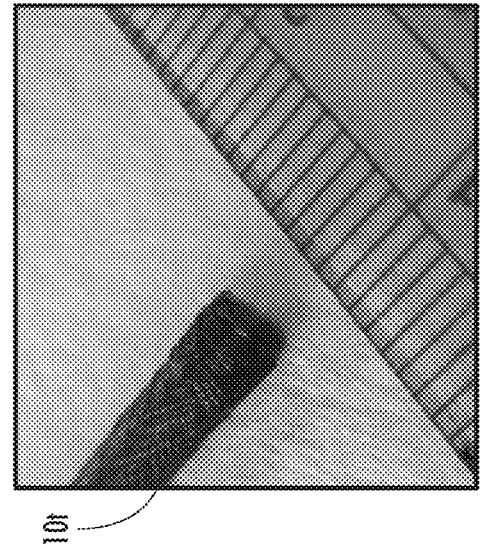

As shown in FIG. 1B, the construct 10 can have a wall 10w with a suitable thickness defined by the at least one collagen fiber 13 and the film layers (where used) and/or other coatings and/or materials placed thereon. The construct can have a uniform or non-uniform stiffness. The construct 10 can have an open through cavity or may be filled or partially filled with a nerve-growth media or other therapeutic material (e.g., an anti-inflammatory, antibiotic and/or the like).

As also shown, the at least one collagen fiber 13 has an angular fiber pattern 13p of repeating intersecting collagen fiber segments along its length. The angular pattern 13p can be defined by a number of revolutions of the at least one fiber 13 about the support member 20 at a given pitch or pitches for at least one layer (typically more than one layer). The support member 20 is used to wrap the at least one collagen fiber around its exterior surface to form a desired shape.

Figure 3A:
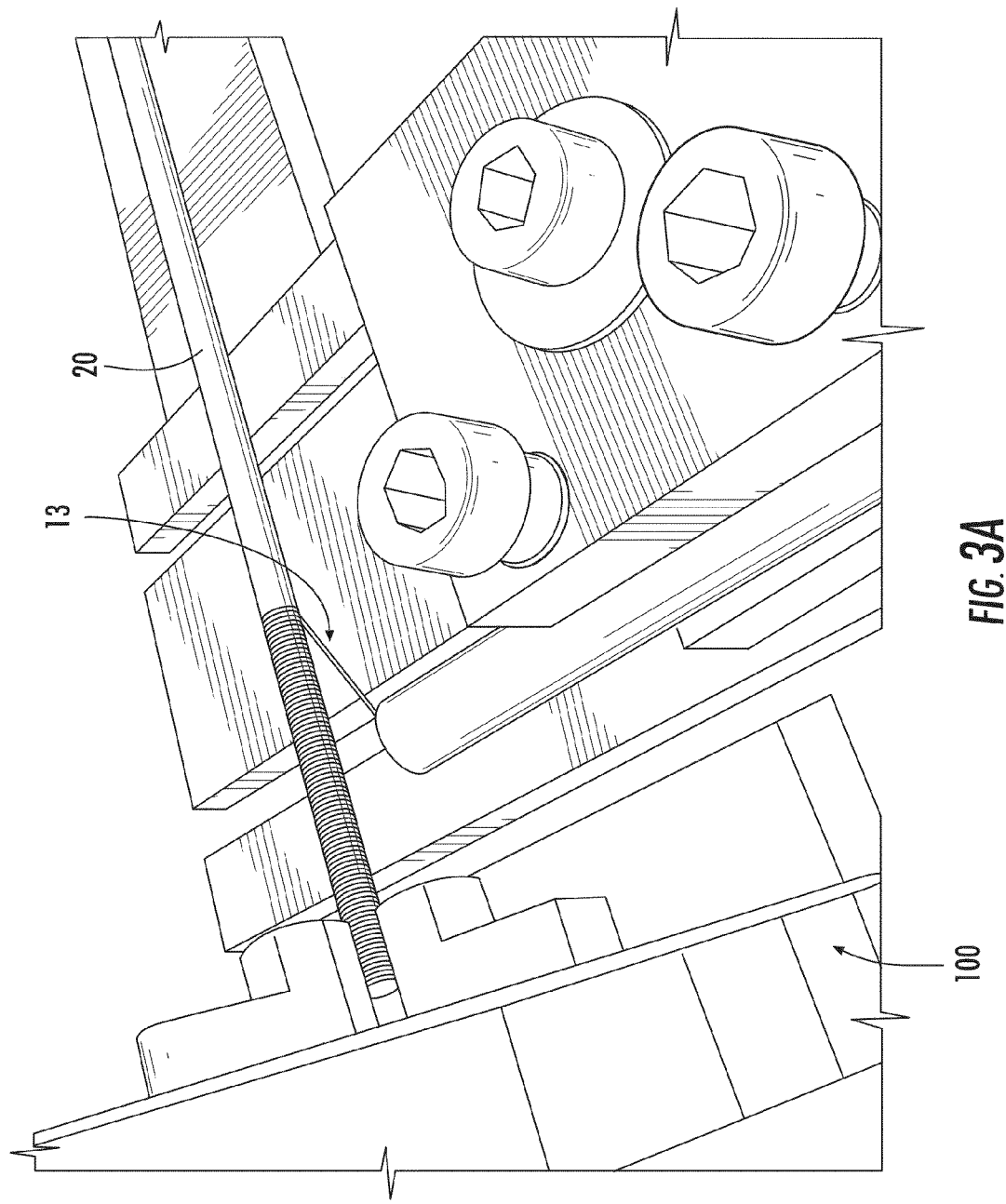
FIG. 3A is a top perspective view of a lathe that can be used to wind collagen fiber(s) onto a tubular support member according to embodiments of the present invention.

The support member 20 can include a lubricious and/or smooth surface, an embossed surface with lower contact surface area, a rough surface, a patterned surface and/or a textured surface, typically of a polymer material. In particular embodiments, the support member 20 can include a ribbed surface 20r (FIG. 19C), which may have a spiral configuration. The ribbed surface of the support member (where used) can provide consistent regions of higher (e.g., ridges) and lower (e.g., valleys) contact surfaces along the length of the support member 20. In other embodiments, the ribs 20r can be configured asymmetrically to vary about the circumference and/or length of the support member 20. The ribs can have the same height and/or thickness or can vary. For example, the ribs 20r can be evenly spaced apart along the length of the support member 20 or the distance between the ribs can vary along the length of the support member 20. In some embodiments, the support member 20 can include an anti-slip surface with ridges or a sleeve can be placed over the support member (not shown) to contact the next layer (e.g., inner film 11 or fiber 13). In some embodiments, the support member 20 comprises Teflon® or other suitable low friction and/or anti-stick material. The support member 20 can be tubular, e.g., cylindrical, as shown in FIGS. 1A, 3A, 3B and 3E or may be substantially flat and rectangular 20' as shown in FIGS. 3C and 3D. Other geometries may also be used, such as, for example, a frustoconical or funnel shape. Typically, the support member 20 is elongate and has a substantially circular, oval, polygonal or other cross-sectional shape. The support member 20 can have a consistent diameter along its length (FIG. 17D) or the support member can be frustoconical or tapered 20f along its length (FIGS. 20A, 20C, 20E, 20F, and 20G).

Figure 19A:
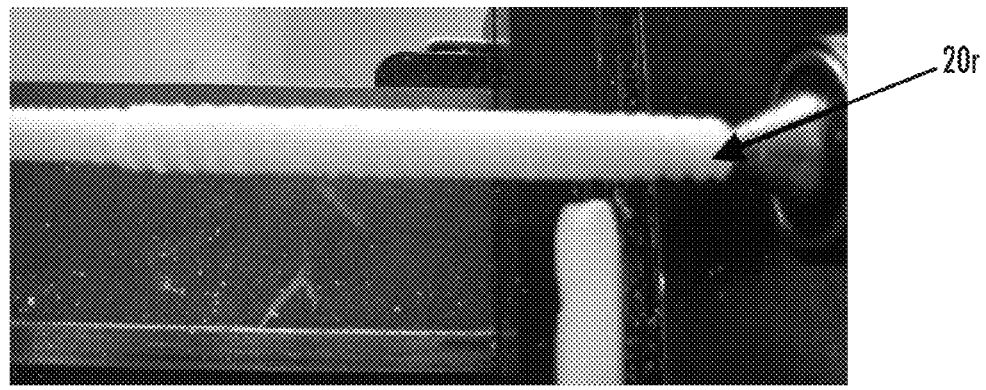
FIG. 19A is a digital photograph of a collagen fiber construct on a ribbed support member according to embodiments of the present invention.
Figure 19B:
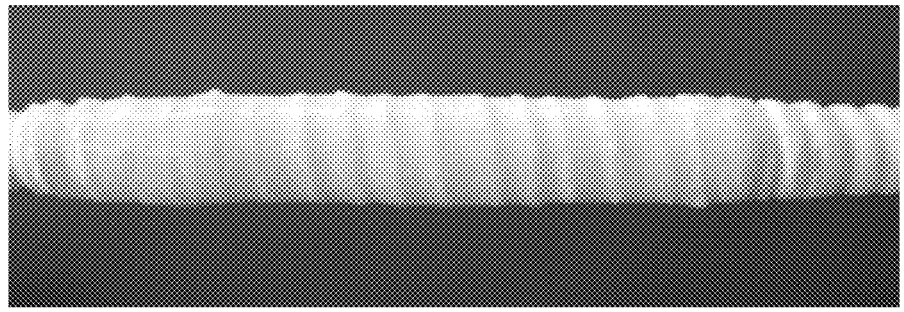
FIG. 19B is a digital photograph of a collagen fiber construct on a support member before cross-linking according to embodiments of the present invention.
Figure 19C:
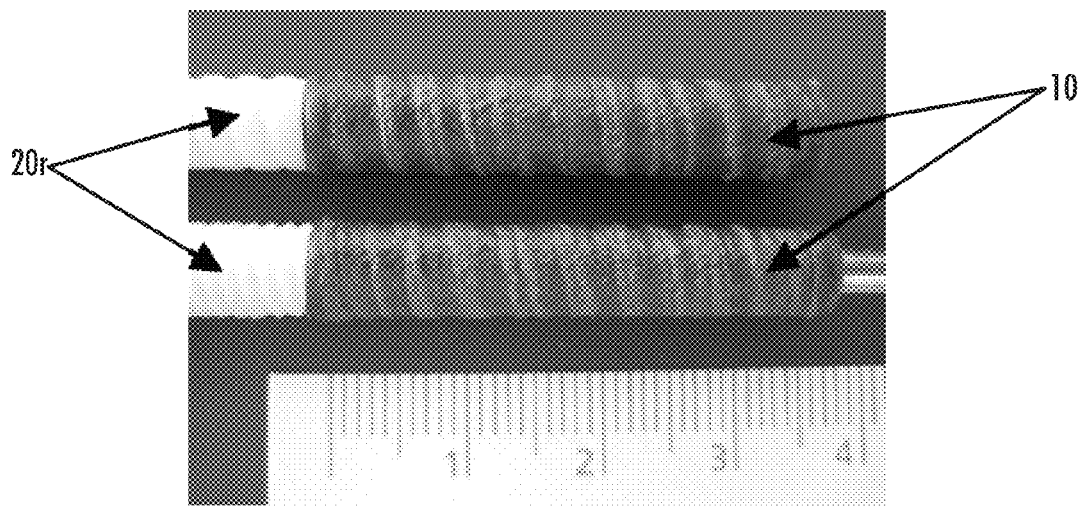
FIG. 19C is a digital photograph of a top view of a prototype of a cross-linked collagen fiber construct with a rough outer and inner surface on a ribbed support member according to embodiments of the present invention.

The design and dimensions of the support member can affect the design and dimensions of the resulting construct 10. For example, a support member with a ribbed surface 20r can provide a construct 10 with a rough inner surface 11r or a support member that is frustoconical or tapered 20f along its length can provide a construct that is similarly tapered (FIG. 19C). In some embodiments, the support member is frustoconical 20f and is about 5 cm in length with a diameter that is between about 3 mm to about 6.5 mm. In certain embodiments, the resulting construct 10 formed on a tapered support member can be particularly suitable for tendons.

The at least one collagen fiber 13 can be organized into various arrays including braids, weaves, knits, parallel arrays, twisted configurations, and the like. The orientation of one or more of the fibers 13 within the resulting material 10 (see, e.g., FIGS. 2A-2D) can be targeted to meet the specific mechanical requirements of the medical application. Fiber density can vary from dense to loose geometries and the numbers and size of the one or more collagen fibers used can vary as well as the thickness of the film to provide specific mechanical properties. The fiber(s) 13 can be continuous length fibers or may be formed by attaching a series of collagen fibers in an end-to-end orientation 13j (FIG. 4).

Figure 8A:
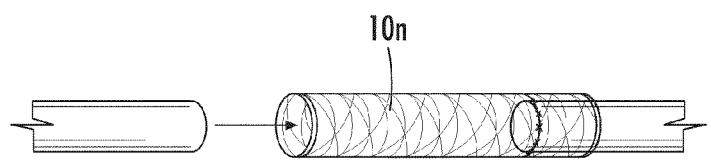
FIG. 8A is a schematic illustration of a collagen fiber medical construct according to embodiments of the present invention.

FIGS. 2A-2D are digital photographs of a prototype of a construct 10. This construct 10 may be particularly suitable as a medical construct, such as an auto and/or allo-graft, a nerve tube or guide 10n (FIG. 8A), or other medical construct. The construct 10 is tubular 10t with an open cavity and has a flexible elastic configuration. The construct 10 can be formed using a single fiber 13 formed in wound multiple layers, the fiber 13 can have a length between about 1-6 m, typically about 5 m. The construct 10 can be formed using a single fiber 13 of a continuous length that is wrapped in several layers about the support member 20. Use of a single fiber 13 can reduce the likelihood of any fraying associated with multiple fibers (such as those wound in one lengthwise direction). The construct 10 can have a length between about 1 cm to about 20 cm (or more), typically between about 5 cm to about 15 cm, and the inner diameter can be between about 1 mm to about 10 mm, typically between about 3 mm to about 20 mm, with the wall thickness being about 0.1 mm to about 3 mm, typically between about 0.1 mm to about 2 mm.

The construct 10 can have reversible elasticity with sufficient rigidity or strength to prevent undue tendon or nerve compression or the like, while allowing flexibility sufficient to allow the construct 10 to spring back into its original shape after being exposed to a strain or tension caused by normal body movement that deforms the shape. The nerve guide 10n can be used for any nerve location, e.g., peripheral nerves (such as in a hand or finger), spinal cord nerves, and the like. The construct 10 can be used for other repairs or treatments as will be discussed further below. The construct 10 is biocompatible (or at least non-cytotoxic) and can provide a desired half-life suitable for its intended function.

The construct 10 and/or the fiber 13 can be cross-linked with a suitable polymerizing material, such as, but not limited to, NDGA, or may be used in a non-cross-linked state. The NDGA cross-linking can increase the strength of the device 10 but may decrease the resiliency, elasticity or flexibility. In some embodiments, the collagen fiber 13 is not cross-linked during the winding process, but may optionally be cross-linked after the winding process (typically after the collagen film has been applied to the outer surface and dried).

Figure 8B:
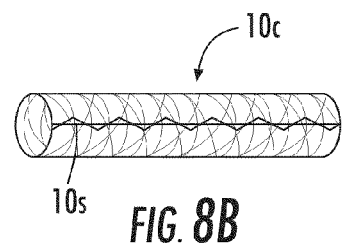
FIG. 8B is a schematic illustration of a collagen fiber medical construct according to embodiments of the present invention.

The support member 20 can be configured to facilitate removal of the construct 10. For example, the construct 10 may be wound tightly against the outer surface of the support member 20 and allowed to dry. The support member 20 can be configured to reduce in cross-sectional size or disassemble with the construct 10 held thereon to allow easy removal of the elongate construct. In some embodiments, the support member 20 can be a multi-piece device that provides this size change. In other embodiments, the support member 20 may be cooled while the construct is heated to provide a size difference. In particular embodiments, the support member 20 can cooperate with an insert 20I (FIG. 3D) that provides the desired size adjustability. In other embodiments, the construct 10 can be removed from the support member without such a size adjustment (e.g., its inner surface may be sufficiently lubricous or a suitable liquid or other material can be used to slide the construct off the support member. In other embodiments, the construct 10 can be cut in a lengthwise (e.g., "X") direction and taken off the support member 20. In some embodiments, the construct 10 may be cut or otherwise separated in a long axis direction with a longitudinal slit 10s and used for a cuff 10c (FIG. 8B) that can be positioned about a nerve or other tissue to protect that tissue (and the cuff may be sutured together along at least a portion of the long axis and/or may be sutured or otherwise anchored into position). The cuff 10c may be configured to provide a snug or alternatively, a non-constricting, encasement for injured tissue such as injured peripheral nerves for protection of the neural environment. The wall of the cuff with the longitudinal slit 10s can be spread open for easy placement over the injured target tissue. The resilience of the collagen conduit allows the cuff to recover and maintain closure once the device is placed around the tissue.

As shown in FIGS. 3A-3B, the construct 10 can be made by winding at least one collagen fiber 13 around a support member 20 using a computer-guided and/or controlled lathe system 100. The lathe system can be configured to rotate the support member 20 and to move the support member back and forth in a length direction to alter the location of the fiber on the support member 20 relative to the introduction point of the fiber (e.g., the fiber introduction point may be stationary). In other embodiments, the fiber(s) 13 can be supplied through a head that moves relative to the support member 20 (e.g., the support member can be stationary) or both the fiber introduction head and the support member may move relative to teach other.

Different size (e.g., diameter) support members 20 can be used depending on the target product. For example, transverse small cross-section support members (e.g., diameter rods) can be used for manufacturing devices for use in vein and artery replacements or repairs, while larger transverse cross-section support members (e.g. diameter rods) can be used to manufacture devices for aortic or large artery replacements or repairs and/or various shunts.

An example of a small lathe 100, typically a micro or miniature lathe, suitable for fabricating embodiments of the constructs is the Model 4410 lathe available from Sherline Products, Inc., having a place of business in Vista, Calif. Two user-selectable inputs can operate the lathe system: one controls the speed that the support member that spins and the other controls the pattern (fiber angle) in which the at least one fiber 13 is laid onto the support member. The operation can be configured so that the fiber is self-pulling from a spool in communication with a channel in the feeder head based on the speed of the spinning support member 20. The lathe 100 can co-wind a plurality of fibers or fiber bundles substantially concurrently about the support member 20.

The at least one collagen fiber 13 can be coated with one or more layers of collagen gel 11, 15 and/or other suitable biocompatible material during and/or after winding the at least one collagen fiber 13 to seal the fiber(s) 13 within the biocomposite material and/or to form a smooth inner and/or outer surface of the construct 10. FIG. 3B illustrates that collagen gel can be applied to the fiber 13 on the support member during the winding. FIG. 3B illustrates that a brush 111 can be used to apply the gel. Other application techniques may be used, such as spray, pour, drop, and the like. The application of the soluble collage gel may be manual or automated and applied by electro-mechanical devices.

The winding can be performed so that at least one layer of the at least one collagen fiber has a substantially constant pitch for at least a major portion of a length thereof or so that at least one layer of the at least one collagen fiber has a variable pitch for at least a major portion of a length thereof.

FIG. 4 illustrates that different configurations of fibers 13 may be used. Examples of fiber configurations include a single fiber $13_1$, a plurality of fibers $13_1 \ldots 13n$ (typically n=2 to 100) that can be concurrently co-wound about the support member 20, a fiber bundle 13b, and a twisted, woven or braided fiber bundle 13t. In some embodiments, a plurality of collagen fibers 13 are twisted, woven, and/or braided together to form a twisted, woven, and/or braided fiber bundle 13t. The twisted, woven, and/or braided fiber bundle 13t can be wound about a support member 20. In certain embodiments, the plurality of collagen fibers 13 comprises between about 3 to about 30 fibers, typically between about 6 to about 15 fibers. For the fiber bundles 13b, 13t, two or more fibers 13 can be grouped together to form the fiber bundle 13b, 13t and that bundle 13b, 13t applied or wrapped about the support member 20, similar to a single fiber. One or more fiber bundles 13b, 13t may be used to form the construct 10. In certain embodiments, a plurality of fibers comprises a fiber bundle 13b, 13t. In some embodiments, the fiber bundle 13b, 13t is combined with between about 6 to about 27 fiber bundles 13b, 13t. Combinations of the different fiber types may also be used for some constructs 10. That is, for example, a twisted fiber 13t can be co-wound with a single fiber $13_1$ and/or a single fiber $13_1$ may be used to form one layer and a twisted 13t to form a different layer, and the like. Exemplary configurations of fibers 13 are described in U.S. Patent Application Publication Nos. 2008/0188933, 2008/0215150, 2008/0200992, 2009/0216233, and 2009/0287308, which are hereby incorporated by reference as if recited in full herein.

The collagen fiber 13 can be wound using various fiber angles (e.g., pitch angles), such as, angles between about 2-70 degrees, typically between about 5-60 degrees, such as, for example, 5, 10, 15, 20, 25, 30, 35, 40, 45, 50, 54 and 55 degrees, or other odd or even numbers between 5-70. Where constructs of multiple layers are used, one layer may have a first pitch and another layer may have a different pitch.

Figure 5A:
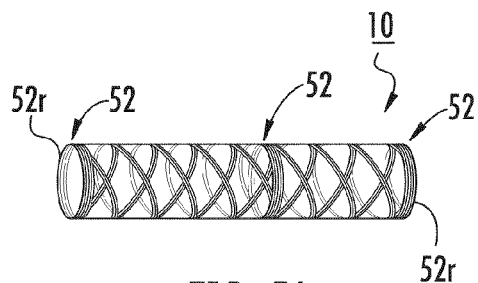
FIG. 5A is a schematic illustration of a tubular construct with segments having increased fiber density according to embodiments of the present invention.
Figure 5B:
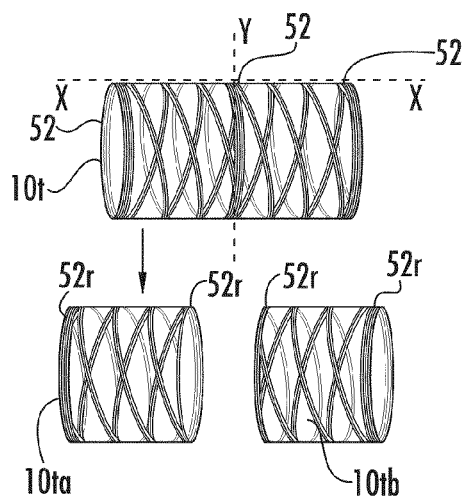
FIG. 5B is a schematic illustration showing that the tubular structure of FIG. 5A can be separated or cut into multiple different components (shown as two) according to embodiments of the present invention.

FIG. 5A illustrates that a construct 10 can be wound with increased fiber density 52 along certain segments, typically forming end rings 52r. This increased fiber density 52 can provide sufficient rigidity to allow a suture to attach thereto. As shown in FIG. 5A, the construct 10 is tubular 10t and may optionally include an increased density segment 52 at an intermediate location. FIG. 5B illustrates that the construct 10 can be used as formed, or may be cut or separated along a Y-axis into two components 10ta, 10tb. For the latter, the intermediate increased density ring 52 can form end rings for the separated construct 10ta, 10tb.

Figure 6A:
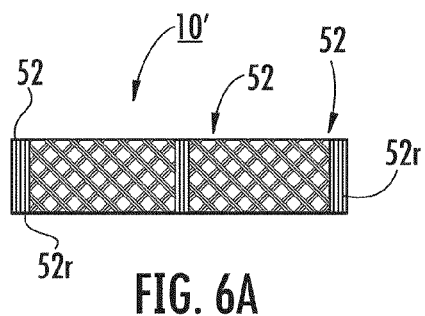
FIG. 6A is a schematic illustration of a substantially planar construct with segments having increased fiber density according to embodiments of the present invention.
Figure 6B:
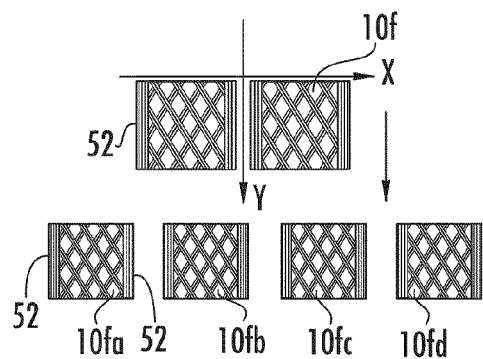
FIG. 6B is a schematic illustration of the construct shown in FIG. 6A illustrating that the construct can be separated into multiple components (shown as four) according to embodiments of the present invention.

FIG. 6A illustrates a construct 10 that is relatively flat 10f and/or rectangular. Again, the construct 10f can optionally include increased fiber density segments 52 that may be suitable for end rings 52r. FIG. 6B illustrates that the construct 10f can be cut along the X-axis and separated into at least two components that form biocompatible patches. The intermediate increased density ring(s) 52, where used, can optionally form end rings 52 for the separated construct 10fa, 10fb, etc.

Figure 7:
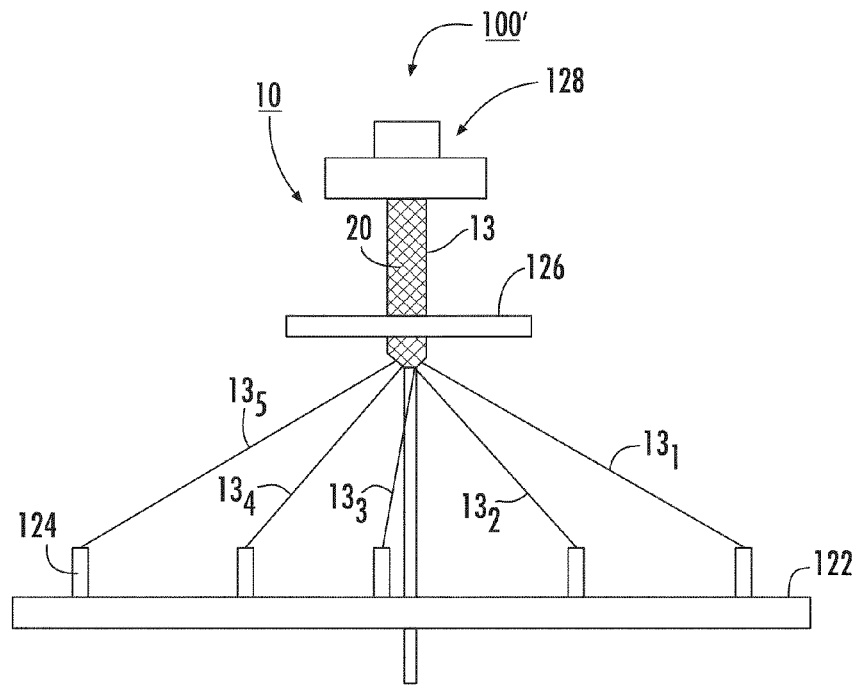
FIG. 7 is a front view of a winding apparatus that can be used to wind (braid) collagen fiber according to embodiments of the present invention.

FIG. 7 illustrates an example of another automated winding system 100' that can be used to form the construct 10. This embodiment uses several fibers 13, each independently wound and/or wrapped to weave or braid the fibers about the support member 20 to form the construct 10. The system 100' includes a plate 122 supporting spindles 124, a forming plate 126, a support member (shown as a cylindrical mandrel) 20 that extends through an aperture in the forming plate 126, and braid puller 128. An exemplary microbraider is believed to be available from Kokubun Ltd of Japan. See also, FIG. 2 and col. 2 of U.S. Pat. No. 7,135,040, the contents of which are hereby incorporated by reference.

The fibers 13 can be wound before or after cross-linking (or not cross-linked at all). If wound before, the fibers can, where desired, be polymerized with any suitable cross-linking materials, to promote collagen organization, such as, for example, NDGA, but other cross-linking materials may be used, including, for example, glutaraldehyde. The (dried) collagen fiber can also be treated with other methods to improve the tensile properties of the fiber. The (dried) collagen fibers 13 can be cross-linked with agents such as glutaraldehyde, formaldehyde, epoxy resins, tannic acid, or any other chemical agent that produces covalent cross-links between collagen molecules within fibrils or between fibrils. Alternatively, the fiber 13 can be treated to induce cross-linking between collagen molecules such as, but not limited to, one or more of a carbodiimide treatment, ultraviolet irradiation either with or without carbohydrates to initiate glycation adducts, and dehydrothermal treatment coupled with any of the aforementioned methods.

Figure 9:
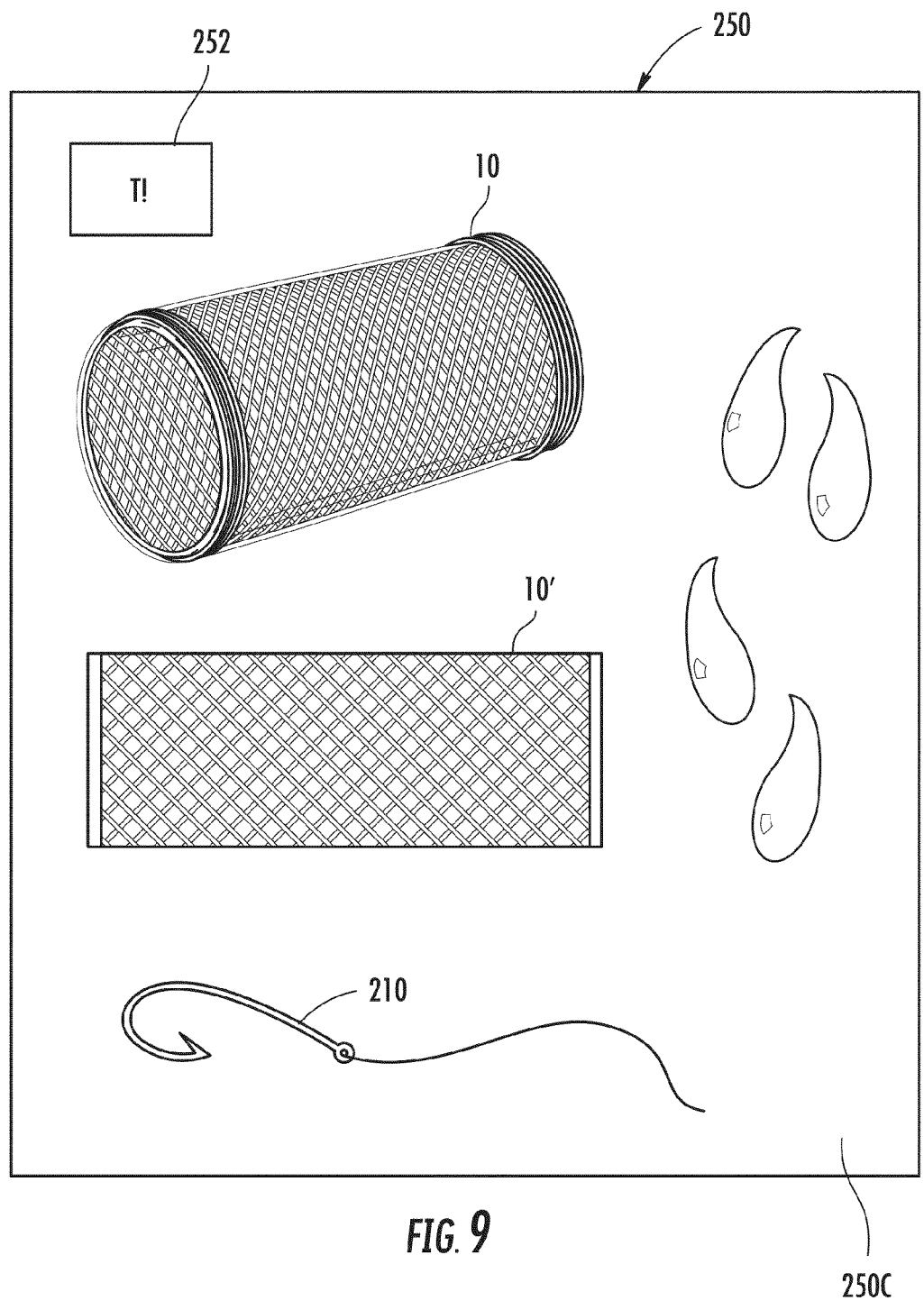
FIG. 9 is a schematic illustration of a medical kit according to embodiments of the present invention.

FIG. 9 illustrates a medical kit 250 that includes a medical device or implant 10 or 10'. The kit 250 may optionally include other components, such as, for example, a container of surgical adhesive, sutures 210, suture anchors, and the like. The device or implant 10, 10' may be held hydrated in a flexible sealed package of sterile liquid 230. The kit 250 may include a temperature warning so that the construct 10, 10' is not exposed to unduly hot temperatures that may degrade the implant. A temperature sensor 252 may optionally be included on the package of the kit to alert the clinician as to any excessive or undue temperature exposure prior to implantation. For example, it may be desirable to hold or store the kit 250 (and implant or device 10, 10') at a temperature that is less than about 37° C. and/or 100° F. prior to implantation. The kit 250 may be packaged in a housing with a temperature controlled or insulated chamber 250c to facilitate an appropriate temperature range.

Figure 10:
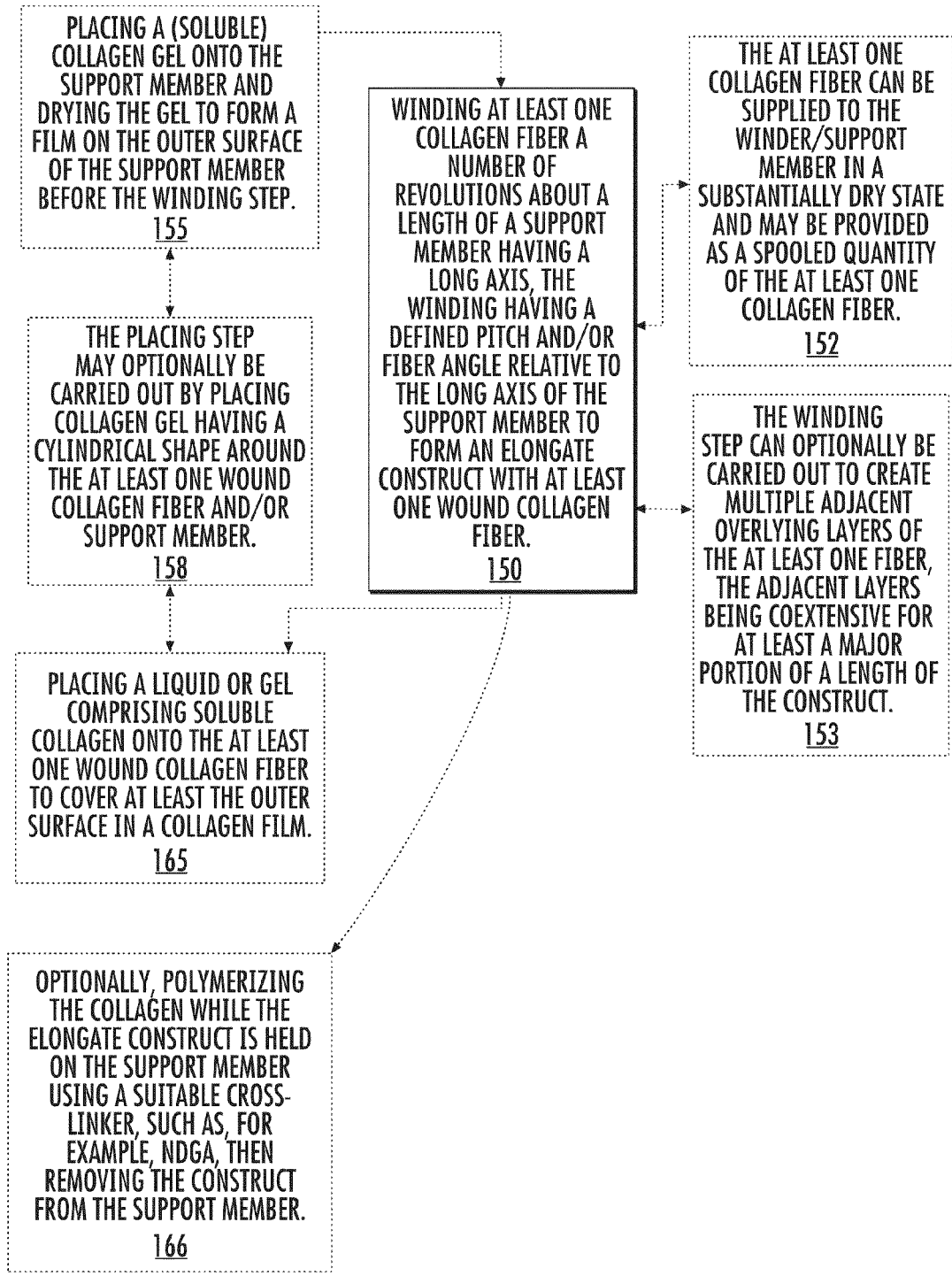
FIG. 10 is a flow chart of operations that can be used to fabricate a construct according to embodiments of the present invention.

FIG. 10 is a flow chart of operations that can be used to carry out embodiments of the present invention. In some embodiments, the at least one collagen fiber is wound a number of revolutions about a length of a support member having a long axis. The winding can have a defined pitch and/or fiber angle relative to the long axis of the support member to form an elongate construct with at least one wound collagen fiber (block 150). The winding step can form multiple overlying layers of the at least one collagen fiber in one or more fiber angles so that the at least one fiber intersects itself at different locations along a length of the construct.

Optionally, a collagen gel can be placed onto the support member and the gel can dry to form a film on the outer surface of the support member before the winding step (block 155). The collagen film can be dried or allowed to dry on the support member (e.g., rod). As the fiber(s) is wound about the support member, a soluble collagen can be applied (e.g., wrapped, painted, sprayed, dripped and the like) onto the fiber(s) and/or support member so that the fiber(s) becomes wet while one or more layers are wound on the lathe.

The at least one collagen fiber can be supplied to the winder/support member in a substantially dry state and may be provided as a spooled (dry) quantity of the at least one collagen fiber (block 152). The fiber(s) can be supplied and wound in a non-cross-linked state.

In some embodiments, the winding step can be carried out to create multiple adjacent overlying layers of the at least one fiber, the adjacent layers being coextensive for at least a major portion of a length of the construct (block 153). A liquid or gel comprising soluble collagen can be placed onto the at least one wound collagen fiber to cover at least the outer surface in a collagen film (block 165).

Optionally, the placing of the collagen gel or liquid is carried out by placing collagen gel having a cylindrical shape around the at least one wound collagen fiber and the support member (block 158).

Optionally, the collagen can be polymerized while the elongate construct is held on the support member using a suitable cross-linker, such as, for example, NDGA, then removing the construct from the support member (block 166).

The winding can be carried out so that the at least one fiber turns about the support member in one of a clockwise or counterclockwise direction along a first lengthwise direction for a first layer, then reverses to travel in an opposing lengthwise direction and continues to turn about the support member in the same clockwise or counterclockwise direction for a second adjacent layer (block 180, FIG. 11).

Alternatively, in particular embodiments, the winding may be carried out so that the at least one collagen fiber turns (is wrapped) about the support member in one of a clockwise or counterclockwise direction along a first lengthwise direction for a first layer, then reverses to travel in an opposing lengthwise direction and turns about the support member in the other clockwise or counterclockwise direction a second adjacent layer.

In some embodiments, the winding step has a first pitch for the winding of the at least one collagen fiber on the first layer and a second smaller or greater pitch for the winding of the at least one collagen fiber on the second layer. In some embodiments, the at least one fiber on the second layer resides between gaps defined by the at least one fiber wound with the defined pitch on the first layer.

Figure 12:
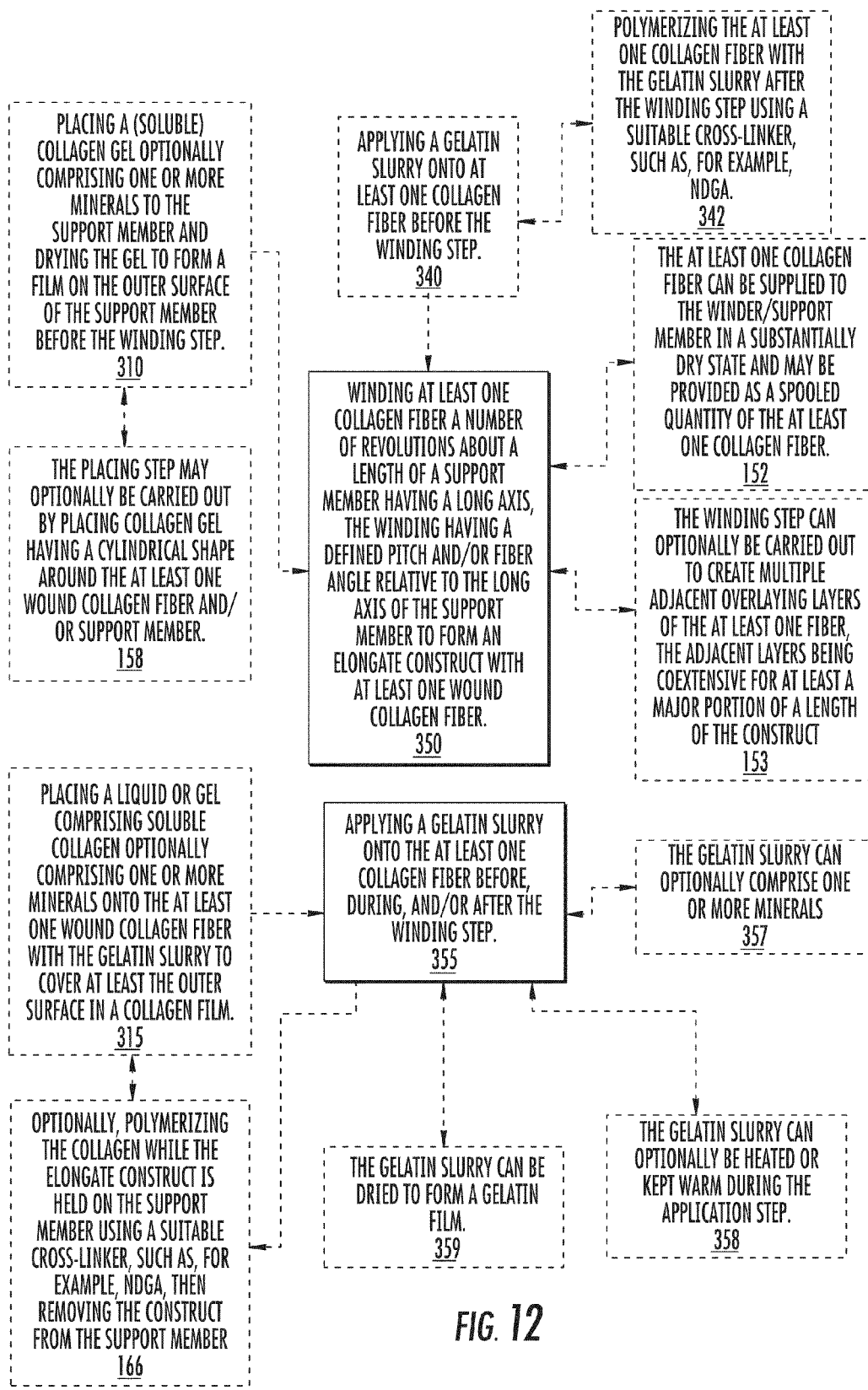
FIG. 12 is a flow chart of operations that can be used to fabricate a construct comprising a gelatin slurry according to embodiments of the present invention.

FIG. 12 is a flow chart of operations that can be used to carry out embodiments of the present invention where a gelatin slurry is applied to the at least one collagen fiber. In certain embodiments, the at least one collagen fiber is wound a number of revolutions about a length of a support member having a long axis. The winding can have a defined pitch and/or fiber angle relative to the long axis of the support member to form an elongate construct with at least one wound collagen fiber (block 350). As the fiber(s) is wound about the support member, a gelatin slurry is applied (e.g., wrapped, painted, sprayed, dripped, dipped, and the like) onto the fiber(s) 13 and/or support member 20 so that the fiber(s) 13 is wetted while one or more layers of the fibers are wound on the lathe (block 355).

The gelatin slurry is typically painted on a fiber during and/or after the fiber is wound on the support member. However, it is contemplated that a collagen fiber can be presprayed, coated, painted, dipped or the like with a gelatin slurry before winding (block 340). The at least one collagen fiber with the gelatin slurry can be polymerized after the winding step with a suitable cross-linker, such as, for example, NDGA (block 342). In some embodiments, a plurality of elongated collagen fibers having a length of between about 1 m to about 100 m are coated with a gelatin slurry comprising one or more minerals.

Also, it is contemplated that a gelatin slurry can be applied to a non-wound collagen fiber construct as well, e.g., braided, twisted, or parallel fibers and the like to form a gelatin film on the collagen fiber construct. The non-wound collagen fiber construct can be cross-linked with a suitable polymerizing material, such as, but not limited to, NDGA, carbodiimide, glutaraldehyde, formaldehyde, tannic acid, isocyanates, and epoxy resins, or may be used in a non-cross-linked state.

As described above, the gelatin slurry can comprise one or more minerals, such as, but not limited to, hydroxyapatite (block 357). During the application of the gelatin slurry, the concentration of the components, e.g. gelatin and/or one or more minerals, can vary. For example, the concentration of the one or more minerals in the gelatin slurry can vary along a length of a support member and/or at different layers. For example, the mineral concentration can be greater at the end of the application step than at the beginning of the application step or vice versa to result in a variation in the mineral concentration along the fiber and/or support member. In certain embodiments a concentration gradient of one or more minerals is established along the fiber and/or support member. Alternatively, the concentration of the gelatin and/or one or more minerals can be higher or lower in certain regions of the fiber and/or support member. The gelatin slurry can be heated before and/or during application to the fiber(s), as described above (block 358).

The thickness of the gelatin intermediate layer 14 can vary depending on the amount or volume of gelatin slurry applied to the at least one collagen fiber, which can vary the wall thickness of a resulting construct. The gelatin intermediate layer 14 comprises at least one collagen fiber, which may be infused, embedded, incorporated, and/or attached to the gelatin slurry, gelatin hydrogel, and/or gelatin film. The gelatin intermediate layer 14 optionally comprising one or more minerals can vary in thickness depending on the amount or volume of gelatin slurry applied to the at least one collagen fiber. As illustrated in FIGS. 18B and 18C, the gelatin intermediate layer comprising one or more minerals 14m can vary in thickness depending on the volume of gelatin slurry applied to the at least one collage fiber. A tube with a thicker wall can provide increased mechanical strength compared to a tube with a thinner wall (FIG. 18G). The application of force to a tube with a thicker wall can, in some embodiments, result in more deformation compared to a tube with a thinner wall (FIG. 18E). When a gelatin slurry is applied to the at least one wound collagen fiber it can be actively and/or passively dried to form a gelatin film (block 359).

The incorporation of one or more minerals into the gelatin slurry can result in the minerals being partially or substantially retained in the construct or tube. The one or more minerals can be partially or substantially retained in the construct. The minerals can be integrated into the construct so that they are substantially retained even when exposed via a cut edge. The construct can retain 50%, 60%, 70%, 75%, 80%, 85%, 90%, 95%, 98%, 99% or 100% of the mineral concentration present in the construct after addition of the gelatin slurry. The mineral concentration can be determined by well known methods. Exemplary methods include, but are not limited to, quantitative chemical analytical techniques such as titrations (e.g., EDTA titrations) and colorimetric methods such as ascorbic acid colorimetric methods, atomic absorption spectroscopy, mass spectrometry such as inductively coupled plasma mass spectrometry (ICP-MS), X-ray fluorescence, X-ray diffraction, and electron probe microanalyzer.

The application of a gelatin slurry optionally comprising one or more minerals onto a collagen fiber(s) can inhibit the tube layers and/or minerals from delaminating, as exemplified in FIGS. 15A-D. The mineral particles can incorporate or integrate into the collagen fiber. The mineral particles can be embedded and/or dissolved in the gelatin hydrogel or gelatin film after cooling and/or drying. The collagen fiber can be embedded or incorporated into the gelatin hydrogel or gelatin film.

Optionally, prior to the winding of the at least one collagen fiber (block 350) a collagen gel optionally comprising one or more minerals can be placed onto the support member and the collagen gel can dry to form a collagen film on the outer surface of the support member before the winding step (block 310). The collagen gel can be dried or allowed to dry on the support member (e.g., rod) either actively or passively. In certain embodiments, a collagen gel comprises at least one mineral. In some embodiments, a collagen gel is placed onto a ribbed support member to form a construct with a rough inner surface. Multiple layers of collagen gel can be placed onto the support member. For example, between about 1 to about 20 layers of collagen gel can be applied, typically between about 1 to about 10 layers of collagen gel can be applied. When multiple layers of collagen gel are applied, the layers can comprise different components and/or the same components present in different concentrations. For example, in some embodiments, between about 1 to about 5 layers of collagen gel with no minerals can be placed onto the support member, followed by between about 1 to about 5 layers of collagen gel with at least one mineral or vice versa.

Optionally, after application of the gelatin slurry, a liquid or gel comprising soluble collagen and optionally one or more minerals can be placed onto the at least one wound collagen fiber with the gelatin slurry to cover at least the outer surface in a collagen film (block 315). In particular embodiments, the soluble collagen comprises at least one mineral and is placed onto the at least one wound collagen fiber with the gelatin slurry to form a construct with a rough outer surface. Multiple layers of soluble collagen can be placed onto the at least one wound collagen fiber with the gelatin slurry. For example, between about 1 to about 20 layers of soluble collagen can be applied, typically between about 1 to about 10 layers of soluble collagen can be applied. When multiple layers of soluble collagen are applied, the layers can comprise different components and/or the same components present in different concentrations. For example, in some embodiments between about 1 to about 5 layers of soluble collagen comprising at least one mineral can be placed onto the at least one wound collagen fiber with the gelatin slurry, followed by between about 1 to about 5 layers of soluble collagen with no minerals or vice versa.

The method can include cutting the construct in an axial direction to form a flat collagen fiber patch. The method can include winding the collagen fibers in a plurality of axially spaced apart segments with increased collagen fiber density, at least some of which are provided as reinforced segments for suturing. The reinforced segments can be formed at end portions of the tube and optionally at one or more intermediate locations therebetween. The methods can produce a nerve guide having sufficient strength and elasticity to withstand buckling and to be able to bend and to elastically return to its original shape after bending to inhibit occlusive pressures or restrictions on nerves.

Embodiments of the invention can be used for a number of different medical applications, including, but not limited to, auto-grafts, allo-grafts, nerve guides, wound bed patches, muscle or organ patches, cardiac patches, valve replacements or repairs, hernia patches, skin patches, burn treatment patches, skin/tissue repair patches or cuffs, blood vessel (artery, vein, and the like) repairs, sleeves that can reside about repairing tendon to prevent or inhibit adhesions, indwelling tubes for delivery of therapeutic agents, ducts such as lymphatic, hepatic, pancreatic and cystic ducts, tubes such as ureter and urethra tubes and the like.

The devices are entirely scalable in all dimensions, length, diameter, wall thickness, relative amount of mineral per collagen, etc. Typically, the devices are tubes that have a length that is between about 5 cm to about 15 cm, a diameter that is between about 3 mm to about 20 mm, and a wall thickness about 0.1 mm to about 2 mm. In particular embodiments, the devices can be used with/for allo-grafts or auto-grafts such as tendon or ligament implants.

Figure 16A:
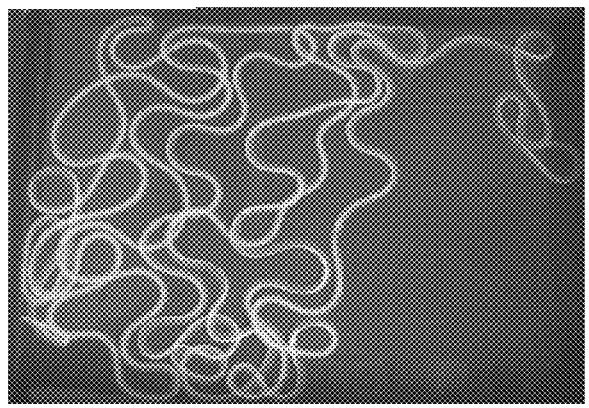
FIG. 16A is a digital photograph of a collagen/hydroxyapatite gel according to embodiments of the present invention.
Figure 16B:
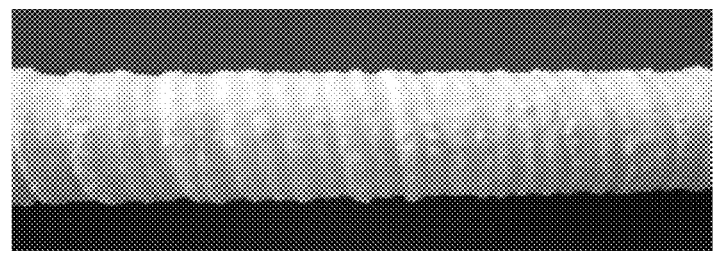
FIG. 16B is a digital photograph of a wet or hydrated/partially hydrated collagen/hydroxyapatite gel wrapped collagen fiber construct comprising a rough outer surface on a support member according to embodiments of the present invention.
Figure 16C:
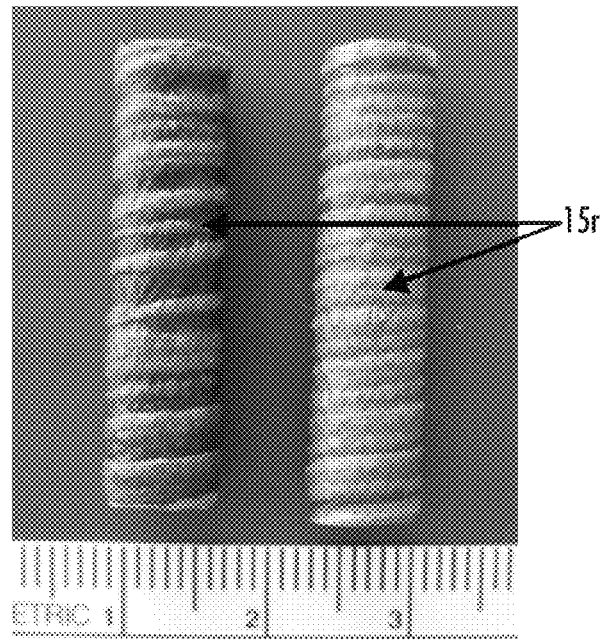
FIGS. 16C-D are digital photographs of a top view of a prototype of a cross-linked collagen fiber construct comprising a rough outer surface according to embodiments of the present invention.
Figure 16D:
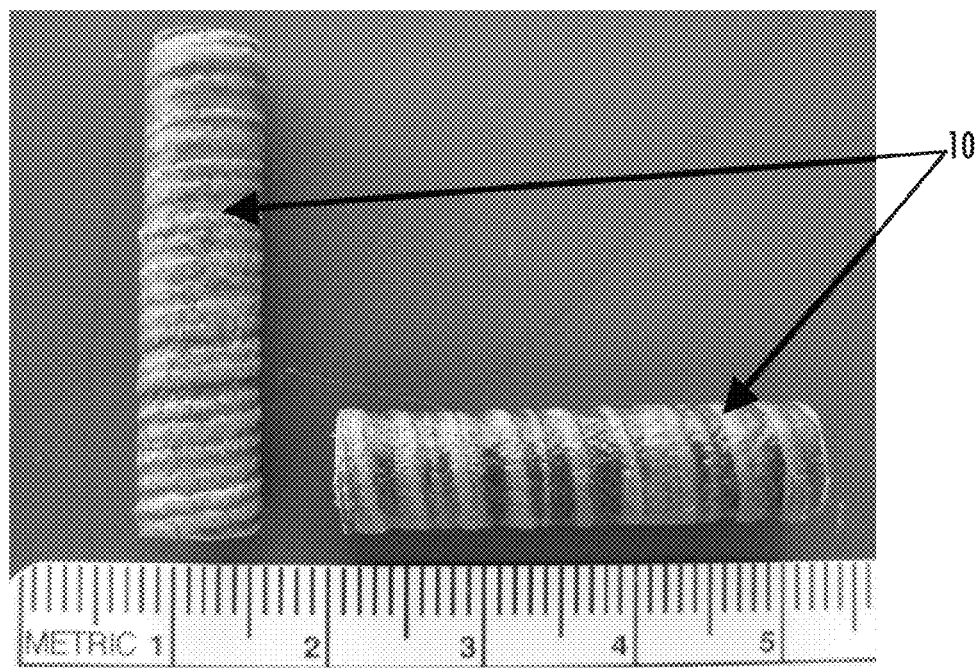
Figure 16E:
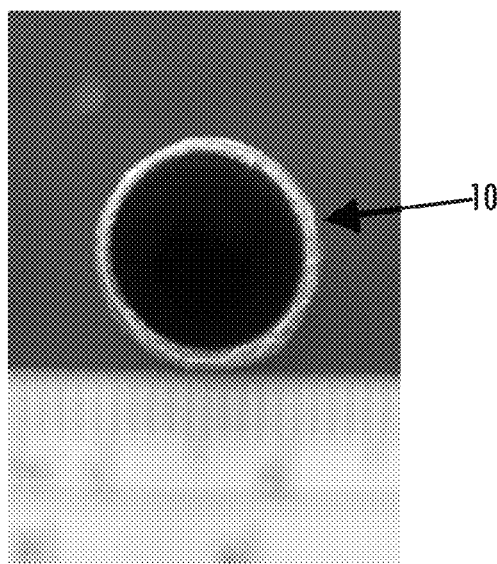
FIG. 16E is a digital photograph of an end view of a prototype of a cross-linked collagen fiber construct comprising a rough outer surface according to embodiments of the present invention.
Figure 17A:
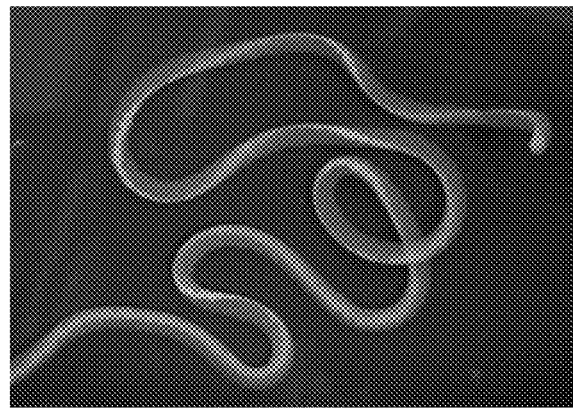
FIG. 17A is a digital photograph of a collagen/hydroxyapatite gel according to embodiments of the present invention.
Figure 17B:
FIG. 17B is a digital photograph of a support member wrapped with an inner collagen gel layer and an intermediate layer comprising at least one collagen fiber and gelatin/hydroxyapatite according to embodiments of the present invention.
Figure 17C:
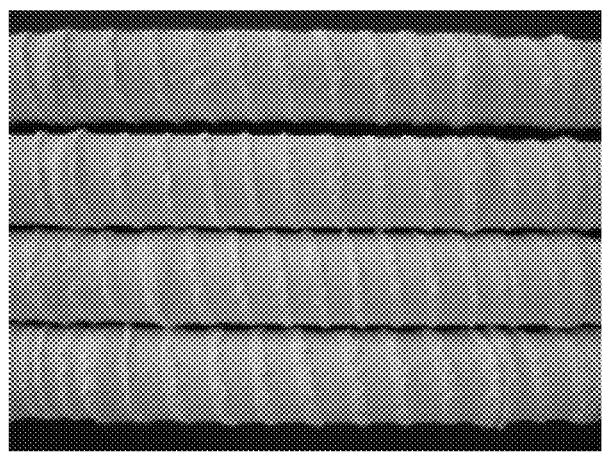
FIG. 17C is a digital photograph of a collagen fiber construct comprising a rough outer surface on a support member according to embodiments of the present invention.
Figure 17D:
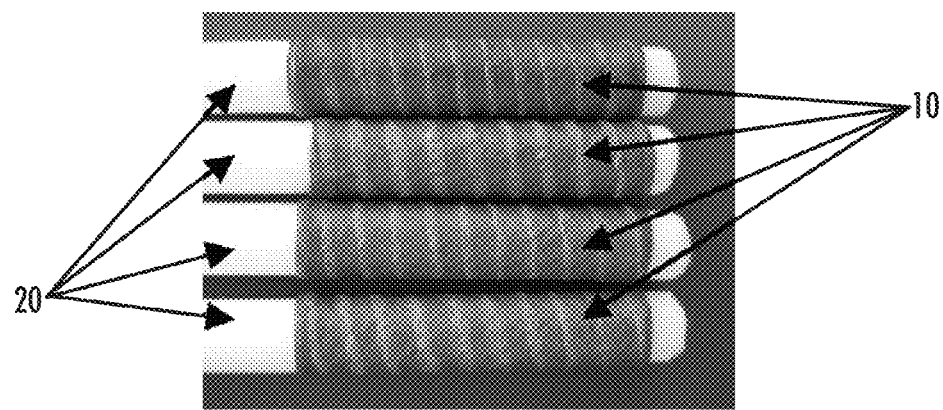
FIG. 17D is a digital photograph of a prototype of a cross-linked collagen fiber construct on a support member comprising a rough outer surface according to embodiments of the present invention.
Figure 17E:
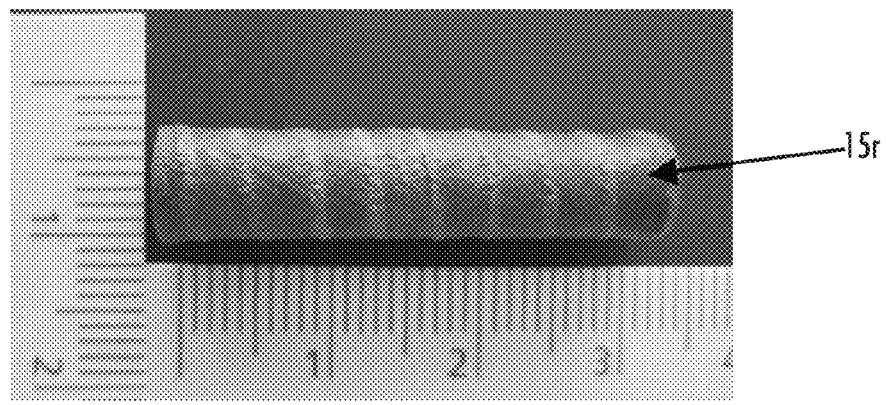
FIG. 17E is a digital photograph of a top view of a prototype of a cross-linked collagen fiber construct comprising a rough outer surface according to embodiments of the present invention.
Figure 19D:
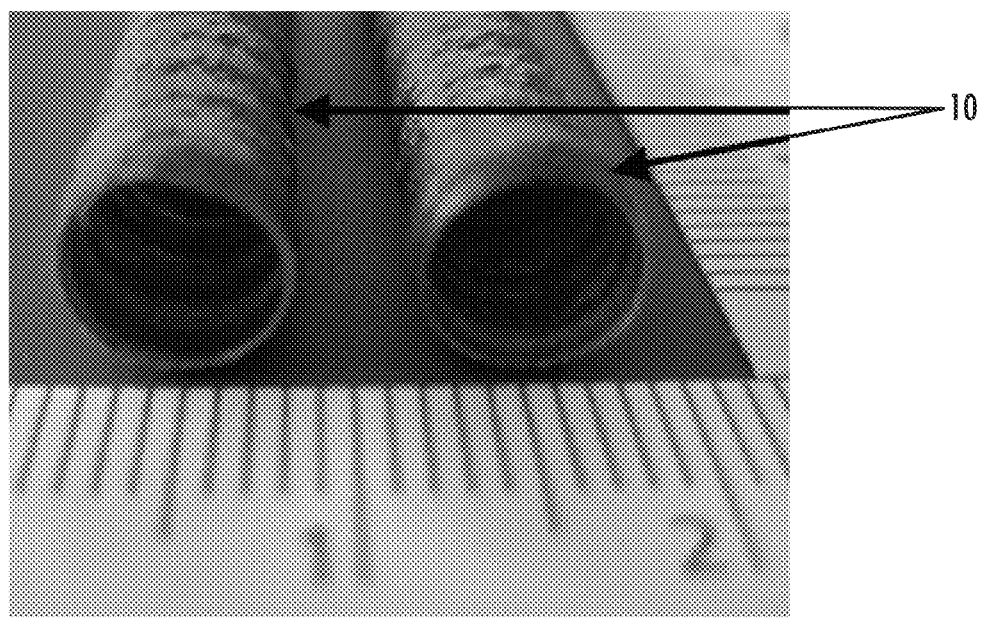
FIG. 19D is a digital photograph of a side perspective view of a prototype of a cross-linked collagen fiber construct with a rough outer and inner surface according to embodiments of the present invention.
Figure 19E:
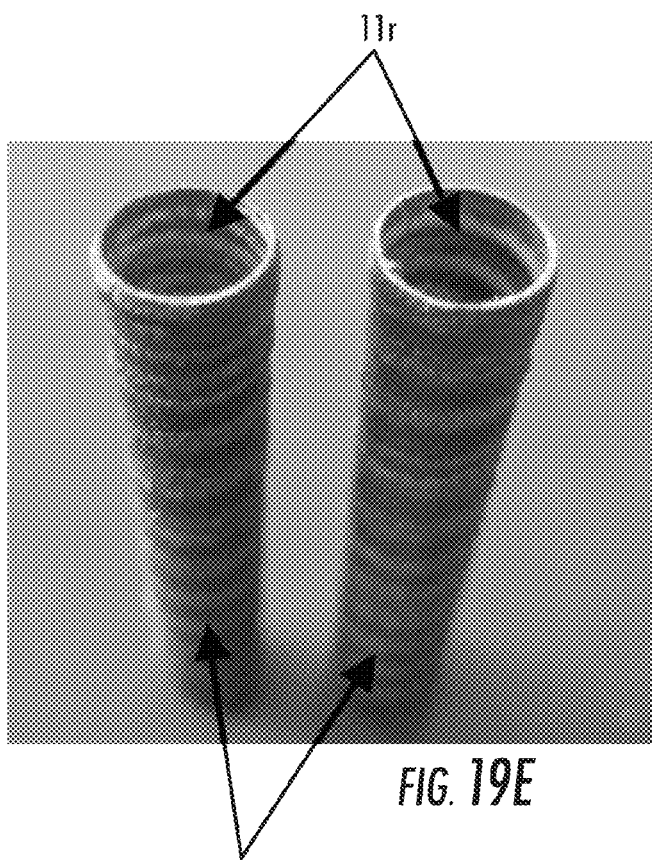
FIG. 19E is a digital photograph of a top perspective view of a prototype of a cross-linked collagen fiber construct with a rough outer and inner surface according to embodiments of the present invention.

The devices can be configured as tubes with rough inner 11$r$ and/or rough outer surfaces 15$r$, as exemplified in FIGS. 16C, 17E, and 19E. The devices can taper in size about its length (FIGS. 20B, 20D, and 20H) or have a substantially constant width (e.g., diameter) (FIGS. 16C-E and 19C-E).

The present invention is explained in greater detail in the following non-limiting Examples.

EXAMPLES

In the following examples the exemplary collagen fiber constructs (e.g., sleeves or tubes) are cross-linked with nor-dihydroguaiaretic acid (NDGA). However, this cross-linking agent is for exemplary purposes only. The present invention is not intended to be limited to cross-linked constructs (i.e., the construct may be used in a non-cross-linked state) or to cross-linked constructs where NDGA is the cross-linking agent. For example, other cross-linking agents, such as, but not limited to carbodiimide, glutaraldehyde, formaldehyde, tannic acid, isocyanates, and epoxy resins, and/or stabilization treatments, such as, but not limited to, one or more of dehydrothermal treatment, glycation, and ultraviolet light may be used in the present invention.

Example 1

FIGS. 2A-2D illustrate exemplary sleeves or tubes of wound NDGA-collagen fibers that may be particularly suitable for medical constructs, such as nerve guides. The inner diameter of the tube can vary between about 1 and 10 mm. The thickness of the wall can vary between about 0.1 and 3 mm. The length of the tube can vary from between about 1 to 6 cm or more.

The tube can be made of dermal collagen that is acid or pepsin soluble. The soluble collagen can be made by neutralizing acid soluble collagen and keeping the soluble collagen at a desired low temperature to maintain the collagen in molecular form, (e.g., about 4° C.). Collagen gels can be produced from acid soluble collagen by neutralization, injection molding in a Teflon® tube of diameter between 0.1 cm to 1.0 cm and incubation for at least about 4 hours at 37° C. The resulting gel can be extruded into deionized water to form a gel cylinder with a diameter between about 0.1 cm to 1.0 cm (and can have a length between about 1-100 m. Collagen concentration of the soluble collagen and collagen gel can be from about 0.1-4% weight per volume. The gel cylinder can be used in the gel form or allowed to dry, actively or passively (suspended in air), to form a collagen fiber having a diameter between about 0.05 mm (average) to about 0.2 mm (average).

The first step to make this prototype tube is to wrap the collagen gel of specified collagen concentration and diameter onto a Teflon® rod of selected diameter. The collagen gel layer was allowed to dry on the rod at room temperature to form a thin layer of collagen film. The thickness of this collagen film can be varied by applying more or less layers of collagen gel, either is a single application of in several applications.

The second step is to wind dry collagen fibers on to the collagen film coated Teflon® rod. The pitch of the fiber relative to the long axis of the tube can be specified. The thickness of the collagen winding can be adjusted, for example, corresponding to the number of layers of fibers that are laid on (and/or the number of fibers bundled together for the winding). During the fiber winding process, soluble collagen is applied (e.g., painted) onto the surface of the laid-on fibers. The thickness of the final soluble collagen layer can be varied to achieve specific thickness. The soluble collagen coated fiber wound cylinder is allowed to dry.

The third step in making the tube is the same as the first step, e.g., to wrap a collagen gel on to the collagen fiber would Teflon® rod and the gel layer is allowed to dry to form a collagen film enwrapping the collagen fiber tube. The thickness of the penultimate collagen film can be varied by the number of layers of wrapped gel.

The dried tube can be used "as-is" (used in a non-cross-linked state and hydrated when in the body or prior to placement in the body), or it can be cross-linked with any agent or action that cross-links the collagen. The (nerve) tube is then taken off the Teflon® rod. In the present example, the tube is cross-linked with nor-dihydroguaiaretic acid (NDGA), see, e.g., U.S. Pat. No. 6,565,960, and U.S. Patent Application Publication No. US-2008-0161917-A1, the contents of which are hereby incorporated by reference as if recited in full herein.

Example 2

Figure 13A:
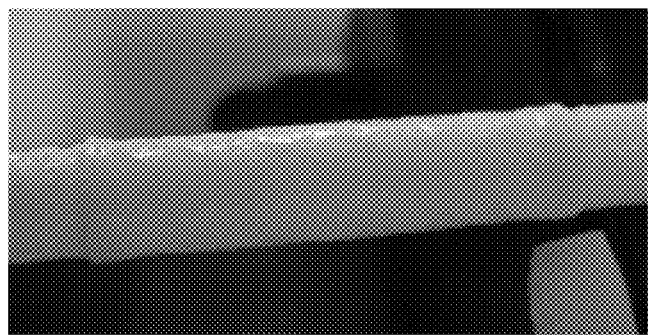
FIG. 13A is a digital photograph of a support member being wrapped with a collagen fiber according to embodiments of the present invention.
Figure 13B:
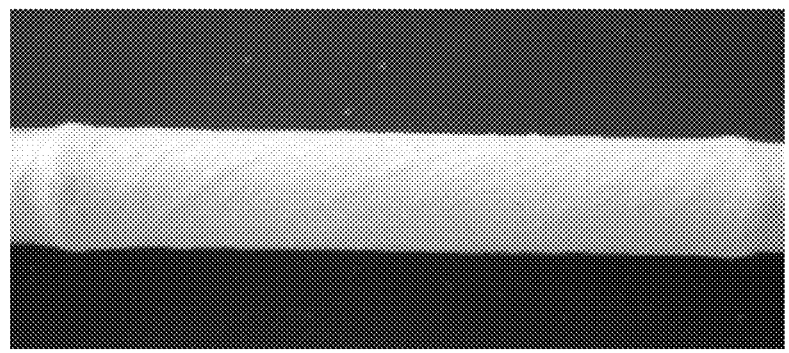
FIG. 13B is a digital photograph of a dry collagen tube comprising an inner collagen gel wrapped with at least one collagen fiber and collagen containing at least one mineral (e.g., hydroxyapatite) on a support member according to embodiments of the present invention.
Figure 13C:
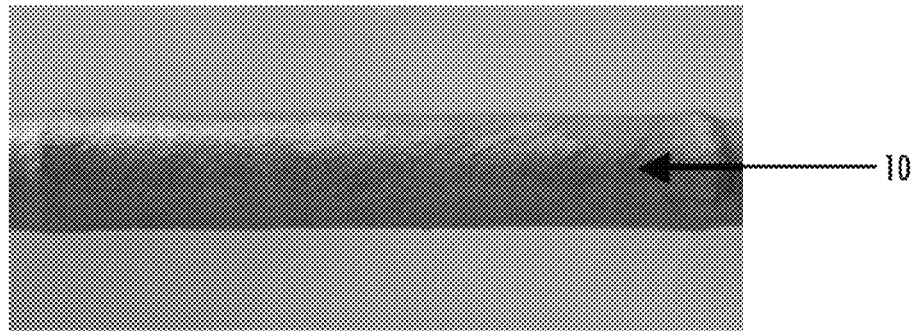
FIG. 13C is a digital photograph of a cross-linked collagen fiber construct (e.g., tube) on a support member according to embodiments of the present invention.
Figure 13D:
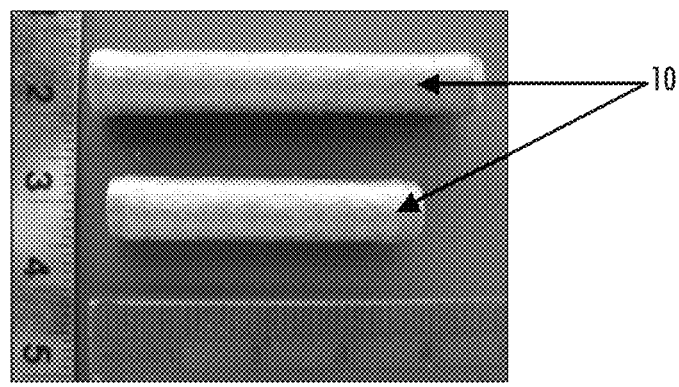
FIG. 13D is a digital photograph of a top view of a prototype of a cross-linked collagen fiber construct prepared with a collagen/hydroxyapatite solution according to embodiments of the present invention.
Figure 13E:
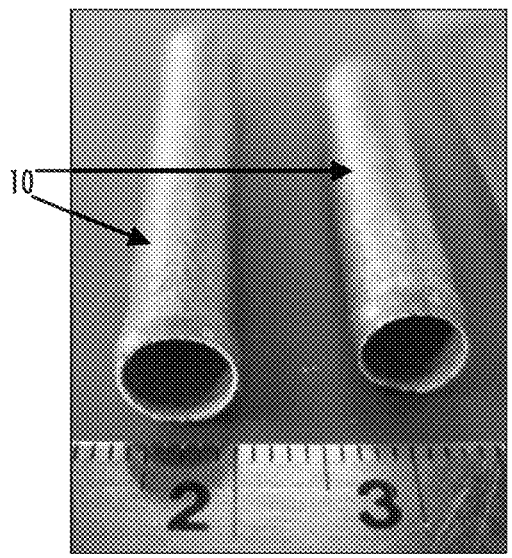
FIG. 13E is a digital photograph of a side perspective view of a prototype of a cross-linked collagen fiber construct prepared with a collagen/hydroxyapatite solution according to embodiments of the present invention.
Figure 13F:
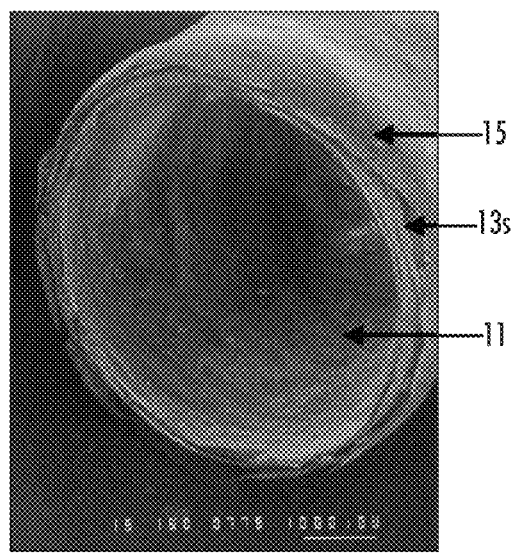
FIG. 13F is a scanning electron microscope image of a cut edge of a collagen fiber construct prepared with collagen/hydroxyapatite painting while winding at least one collagen fiber according to embodiments of the present invention.

FIGS. 13A-F depict various stages in the formation of an exemplary collagen fiber construct of the present invention that comprises an intermediate layer comprising at least one wound collagen fiber and one or more layers of collagen/HA applied to the collagen fiber. This exemplary embodiment may be particularly suitable for medical constructs. Hydroxyapatite (HA) can be mixed in a neutralized collagen solution at pH 7.2 at a very high concentration to form a collagen/HA solution. A 7 mm Teflon® rod can be wrapped with between about 5 to about 6 layers of collagen gel and dried. Uncrosslinked collagen fibers can be wound on the collagen coated Teflon® rod. FIG. 13A is a digital photograph of the rod being wrapped with the uncrosslinked collagen fibers. While the collagen fiber is being wound, the collagen/HA solution can be painted along the fiber winding. FIG. 13B is a digital photograph of the dry collagen tube comprising the inner collagen gel wrapped with the collagen fiber and painted with the collagen/HA solution on the rod. Eight layers of collagen gel can be wrapped on the fibers wound on the Teflon® rod, The tube can then be crosslinked in 100 mL standard NDGA solution for approximately 24 hours and then washed by phosphate buffer pH 9 and 70% ethanol for 1 hour each. FIG. 13C is a digital photograph of the completed tube comprising the inner collagen gel wrapping, the wound collagen fiber with the collagen/HA, and the outer collagen gel wrapping that has been cross-linked with NDGA on the rod. The tube can be air dried and taken off the Teflon® rod. FIGS. 13D-F illustrate the completed exemplary NDGA crosslinked collagen fiber constructs (e.g., tubes or sleeves).

Example 3

Figure 14A:
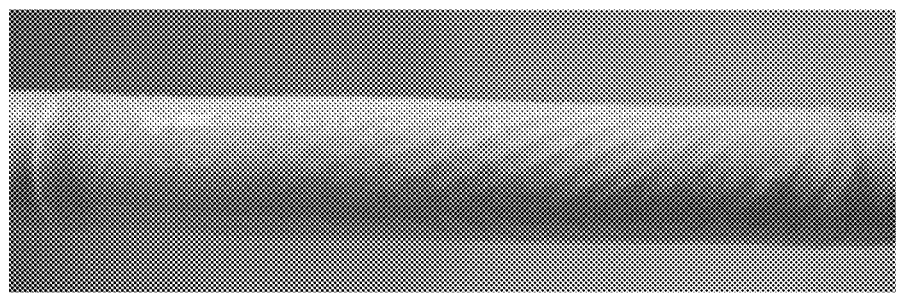
FIG. 14A is a digital photograph of a wet or hydrated/partially hydrated collagen fiber construct comprising an inner collagen gel layer wrapped with an intermediate layer comprising at least one collagen fiber and gelatin/hydroxyapatite, and an outer collagen gel layer comprising a mineral on a support member according to embodiments of the present invention.
Figure 14B:
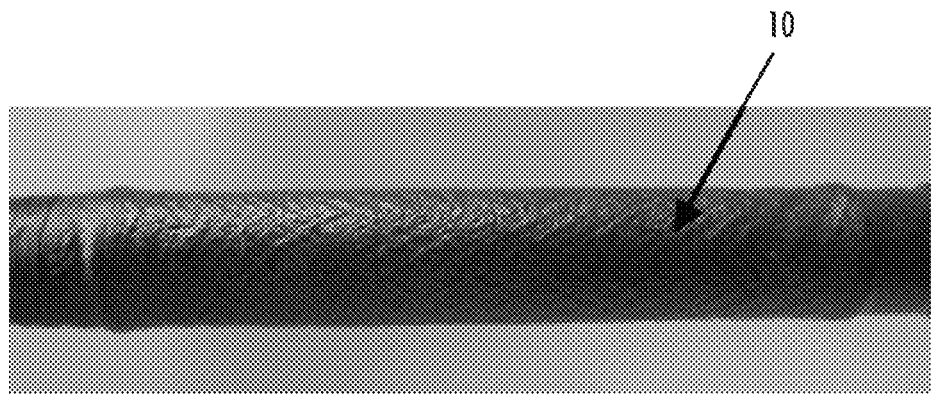
FIG. 14B is a digital photograph of the construct of FIG. 14A, but cross-linked on the support member according to embodiments of the present invention.
Figure 14C:
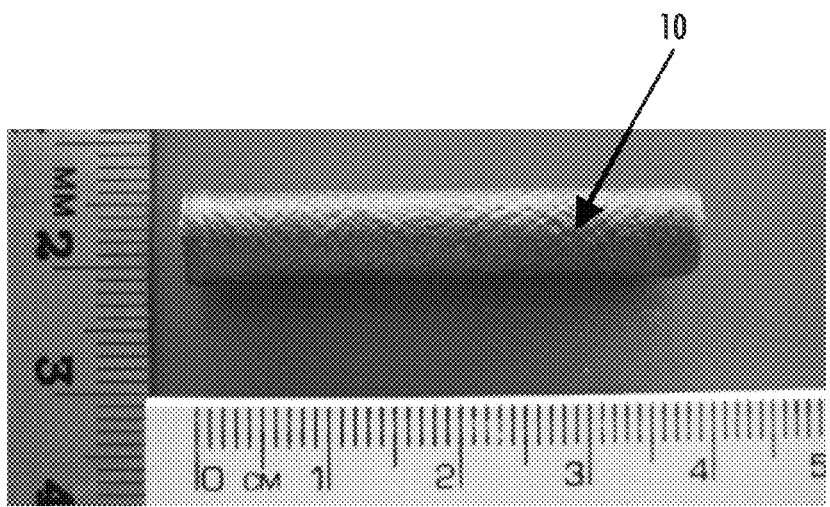
FIG. 14C is a digital photograph of a top view of a prototype of a cross-linked collagen fiber construct prepared with a gelatin/hydroxyapatite solution according to embodiments of the present invention.
Figure 14D:
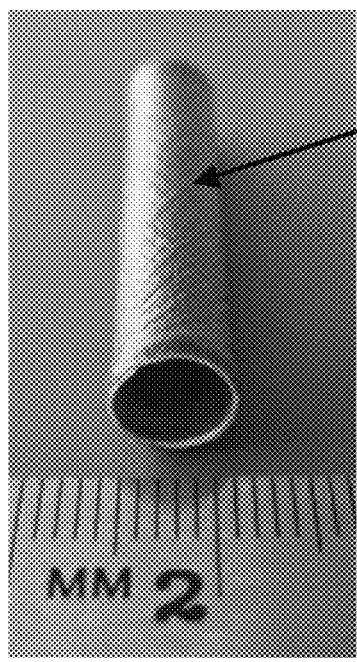
FIG. 14D is a digital photograph of a side perspective view of a prototype of a cross-linked collagen fiber construct prepared with a gelatin/hydroxyapatite solution according to embodiments of the present invention.
Figure 14E:
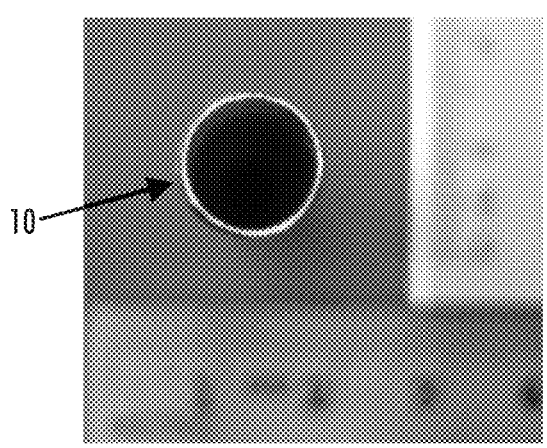
FIG. 14E is a digital photograph of an end view of a prototype of a cross-linked collagen fiber construct prepared with a gelatin/hydroxyapatite solution according to embodiments of the present invention.
Figure 14F:
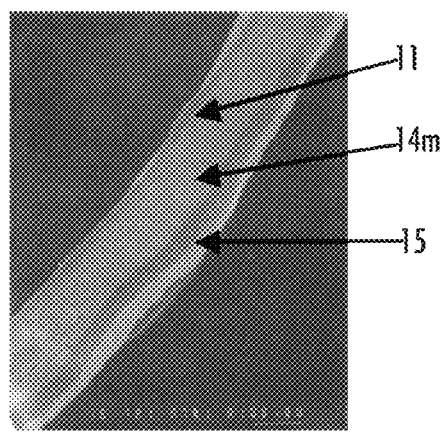
FIG. 14F is a scanning electron microscope image of a cut edge of a collagen fiber construct demonstrating the collagen gel layers and the gelatin/hydroxyapatite layer according to embodiments of the present invention.
Figure 14G:
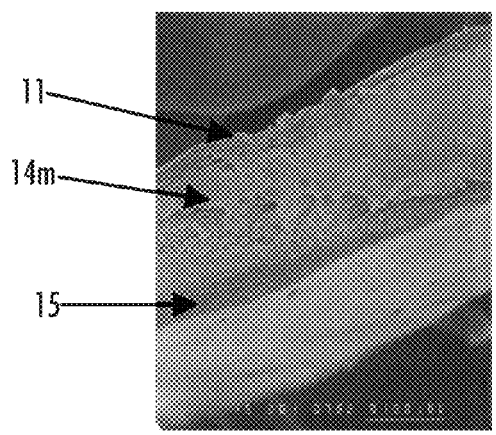
FIG. 14G is an enlarged scanning electron microscope image of a cut edge of a collagen fiber construct demonstrating the collagen gel layers and the gelatin/hydroxyapatite layer according to embodiments of the present invention.

FIGS. 14A-G depict various stages in the formation of an exemplary collagen fiber construct of the present invention that comprises an intermediate layer comprising at least one wound collagen fiber and one or more layers of gelatin/HA applied to the collagen fiber. This exemplary embodiment may be particularly suitable for medical constructs. 1 gram of hydroxyapatite can be mixed in 5 mL of 3% Sigma gelatin A solution, to yield a gelatin/HA solution with a concentration of HA particles of 20%. A 7 mm Teflon® rod can be wrapped with 5-6 layers of collagen gel and dried. Uncrosslinked collagen fibers can be wound on the collagen coated Teflon® rod, meanwhile the gelatin/HA solution can be painted along the fiber winding. Eight layers of collagen gel can be wrapped on the fibers wound on the Teflon® rod. FIG. 14A is a digital photograph of the completed device still wet on the rod with the three layers: the inner collagen gel layer, the intermediate layer comprising the wound collagen fiber and gelatin/hydroxyapatite, and the outer collagen gel layer. The tube can be crosslinked in 100 mL standard NDGA solution for approximately 24 hours, and then washed by phosphate buffer pH 9 and 70% ethanol for 1 hour each. FIG. 14B is a digital photograph of the completed device that has been cross-linked on the rod with NDGA. The tube can be air dried and taken off the Teflon® rod. FIGS. 14C-G illustrate the completed exemplary NDGA crosslinked collagen fiber constructs (e.g., tubes or sleeves).

Example 4

FIGS. 16A-E depict various stages in the formation of an exemplary collagen fiber construct of the present invention that comprises a rough outer surface. This exemplary embodiment may be particularly suitable for medical constructs. Hydroxyapatite can be mixed in neutralized collagen solution (pH 7.2) at a concentration of 1% (300 mg/30 mL=1 g/100 mL) for wrapping gel (collagen/HA), such collagen/HA gel is depicted in FIG. 16A. Hydroxyapatite can be mixed in 2% gelatin at a concentration of 10% for painting purposes (gelatin/HA, total 5 mL for 3 tubes, 500 mg HA/5 mL 2% Gelatin=10 g/100 mL).

A 6.35 mm (¼") Teflon® rod can be wrapped with 6 layers of Devro collagen gel and dried. Uncrosslinked collagen fibers can be wound on the collagen coated Teflon® rod, meanwhile the warm gelatin/HA solution (50-55° C.) can be painted along the fiber winding under heat. The painting with the gelatin/HA solution can be continued until finish a 5 mL solution for all 3 tubes. Two layers of collagen/HA gel can be wrapped on the fibers wound on the Teflon® rod. FIG. 16B is a digital photograph of the wet collagen/HA gel wrapped collagen fiber construct comprising a rough outer surface on the rod. Then, four layers of "pure" collagen gel (i.e., collagen gel with collagen, but no additional components or minerals) can be wrapped on the tubes. The tubes can be crosslinked in standard NDGA solution for approximately 24 hours, and then washed by phosphate buffer pH 10.3 (or pH 9) and 70% ethanol for 1 hour each. The construct can be air dried and taken off the Teflon® rod (or hydrated if the construct cannot be taken off). FIGS. 16C-E illustrate the completed exemplary NDGA crosslinked collagen fiber constructs (e.g., tubes or sleeves).

Example 5

FIGS. 17A-F depict various stages in the formation of an exemplary collagen fiber construct of the present invention that comprises a rough outer surface. This exemplary embodiment may be particularly suitable for medical constructs. Hydroxyapatite can be mixed in neutralized collagen solution (pH 7.2) at a concentration of 1% for wrapping gel (collagen/HA, Devro 0.5% collagen, dilute with DI salt solution at 1:1, adjust pH 7.22, 900 mg HA/90 mL neutralized collagen solution=1 g/100 mL=1%). The collagen/HA wrapping gel is depicted in FIG. 17A. Hydroxyapatite can be mixed in 2% gelatin at 10% for painting purpose (gelatin/HA, total 40 mL for 24 tubes, 4 g HA/40 mL 2%, Gelatin=10 g/100 mL=10%). Collagen/HA gel can be formed in the incubator at 37° C. for 4 hours before extruded into DI water, which is the same as the procedure for forming general collagen gel. Gelatin/HA painting solution can be kept in a water bath at 45-50° C. to warm up the gelatin during fiber winding and painting process.

Figure 17F:
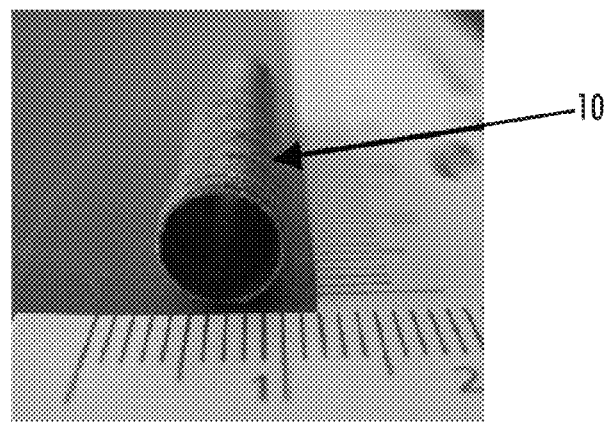
FIG. 17F is a digital photograph of a side perspective view of a prototype of a cross-linked collagen fiber construct comprising a rough outer surface according to embodiments of the present invention.

A 6.35 mm (¼") Teflon® rod can be wrapped with 4 layers of Devro collagen (0.25%) gel and dried. Uncrosslinked collagen fibers can be wound on the collagen coated Teflon® rod, meanwhile the warm gelatin/HA solution (50° C.) can be painted along the fiber winding. The average volume of gelatin/HA painting solution used can be approximately 1.5 mL per tube. FIG. 17B is a digital photograph of the rod wrapped with the inner collagen gel layer and the intermediate layer comprising the collagen fiber painted with gelatin/hydroxyapatite. The tube can then be dried. One layer of collagen/HA gel can be wrapped on the fibers wound on the Teflon® rod. FIG. 17C is a digital photograph of the collagen fiber construct comprising the rough outer surface on the rod. Then, three layers of pure collagen gel can be wrapped on the tube and air dried. The tube can be crosslinked in standard NDGA solution for approximately 24 hours, and then washed by phosphate buffer pH 10.3 (or pH 9) and DI water. The tube can be air dried and taken off the Teflon® rod (or hydrated if the tubes cannot be taken off). FIGS. 17D-F illustrate the completed exemplary NDGA crosslinked collagen fiber constructs (e.g., tubes or sleeves).

Example 6

Figure 18A:
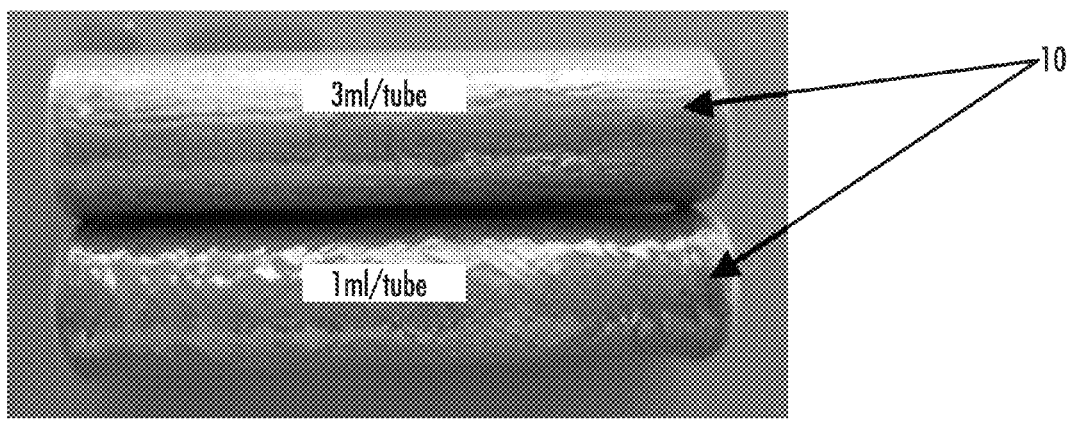
FIG. 18A is a digital photograph of a prototype of a cross-linked collagen fiber construct prepared with about 1 mL/tube of gelatin/hydroxyapatite solution or about 3 mL/tube of gelatin/hydroxyapatite solution according to embodiments of the present invention.
Figure 18B:
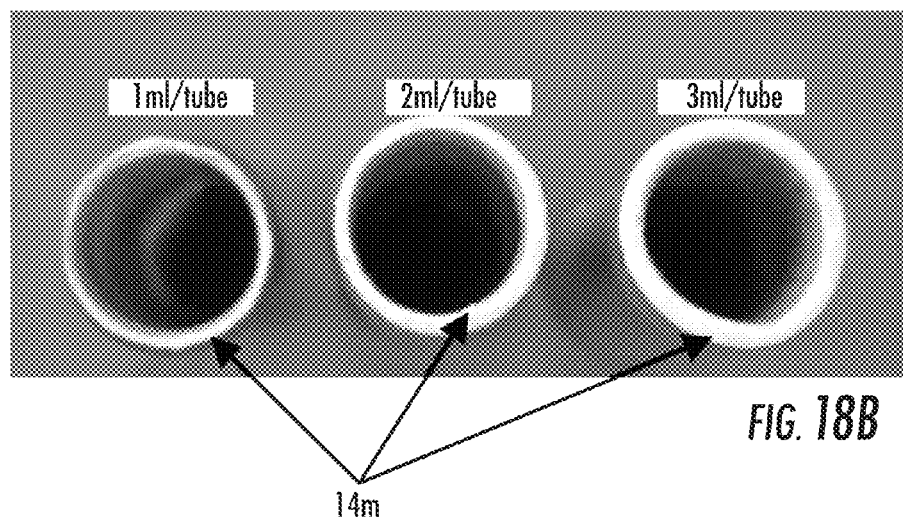
FIG. 18B is a digital photograph of a prototype of a cross-linked collagen fiber construct prepared with about 1 mL/tube, about 2 mL/tube, or about 3 mL/tube of gelatin/hydroxyapatite solution according to embodiments of the present invention.
Figures 18C, 18D:
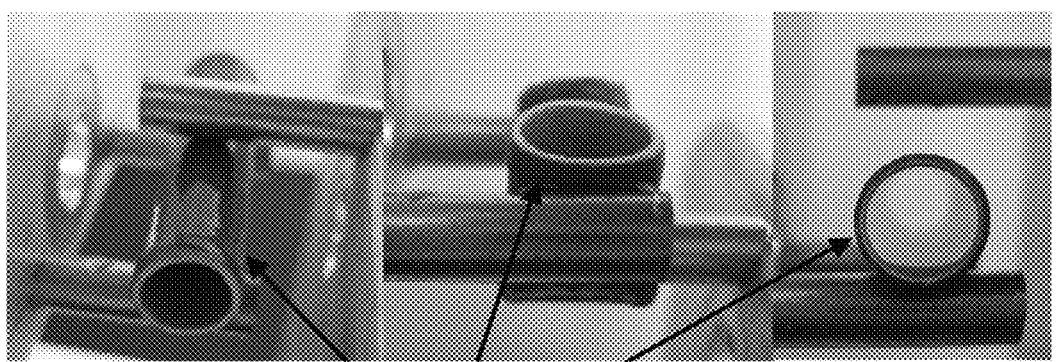
FIG. 18C is a chart displaying the wall thickness (mm) of exemplary collagen fiber constructs prepared with about 1 mL/tube, about 2 mL/tube, or about 3 mL/tube of gelatin/hydroxyapatite solution and the ratio of wall thickness to the outer radius of the tube according to embodiments of the present invention.
FIG. 18D is a set of digital photographs of a prototype of a collagen fiber construct during a 3-point bending test according to embodiments of the present invention.

FIGS. 18A-B illustrate exemplary sleeves or tubes of wound NDGA-collagen fibers that may be particularly suitable for medical constructs. A 6.35 mm (¼") Teflon® rod can be wrapped with 6 layers of Devro collagen gel and dried to provide a tube with an inner diameter of 6.35 mm. Uncrosslinked collagen fibers can be wound on the collagen coated Teflon® rod, meanwhile a warm gelatin/HA solution (50-55° C.) can be painted along the fiber winding under heat and until dry. The volume of gelatin/HA solution used for painting can be 1 mL/tube, 2 mL/tube, or 3 mL/tube. Six layers of pure collagen gel can be wrapped on the tubes.

The wall thickness (mm) of exemplary 1 mL/tubes, 2 mL/tubes, and 3 mL/tubes is displayed in FIG. 18C along with the ratio of wall thickness to the outer radius of the tube for these tubes. The amount of deformation or deflection (mm) in exemplary 1 mL/tubes, 2 mL/tubes, and 3 mL/tubes was measured using a 3-point bending test, as exemplified in FIGS. 18D-G. Observations from this test were that in general, the thicker the wall, the more permanent deformation was caused if the bending test kept pressing at the same point.

Example 7

FIGS. 19A-E depict various stages in the formation of an exemplary collagen fiber construct of the present invention that comprises a rough inner and outer surface. This exemplary embodiment may be particularly suitable for medical constructs. Hydroxyapatite can be mixed in neutralized collagen solution (pH 72) at concentration of 1% for wrapping gel (collagen/HA, Devro 0.5% collagen, dilute with DI salt solution at 1:1, adjust pH 7.22, 500 mg HA/50 mL neutralized collagen solution=1 g/100 mL=1%). Hydroxyapatite can be mixed in 2% gelatin at 10% for painting purpose (gelatin/HA, total 4 mL for 4 tubes, 400 mg HA/4 mL 2% Gelatin=10 g/100 mL=10%). Collagen/HA gel can be formed in the incubator at 37° C. for 4 hours before extruded into DI water, which is the same as the procedure for forming general collagen gel. Gelatin/HA painting solution can be kept in a water bath at 45-50° C. to warm up the gelatin during fiber winding and painting process.

A 6.35 mm (¼") spiral Teflon® rod can be wrapped with 4 layers of general Devro collagen (0.25%) gel, dried, and wrapped with 2 layers of collagen/HA gel. Uncrosslinked collagen fibers can be wound on the collagen coated Teflon® rod, meanwhile a warm gelatin/HA solution (50° C.) can be painted along the fiber winding. The average volume of gelatin/HA painting solution used can be approximately 1-1.5 mL per tube. The tube can then be air dried. Two layers of collagen/HA gel can be wrapped on the fibers wound on the Teflon® rod and then 4 layers of general Devro collagen gel can be wrapped on the fibers wound on the Teflon® rod. FIGS. 19A and 19B are digital photographs of the collagen fiber construct with a rough inner and outer surface on a spiral rod before cross-linking. The tube can be crosslinked in standard NDGA solution for approximately 24 hours, and then washed with phosphate buffer pH 10.3 (or pH 9) and DI water for 1 hour each. FIG. 19C is a digital photograph of the cross-linked collagen fiber construct with a rough inner and outer surface on the spiral rod. The tube can be air dried and "screwed" off the Teflon® spiral rod (or hydrated if the tube cannot be taken off) or split or cut along a portion or all of its length. FIGS. 19D-E illustrate the completed exemplary NDGA crosslinked collagen fiber constructs (e.g., tubes or sleeves).

Example 8

Figure 20A:
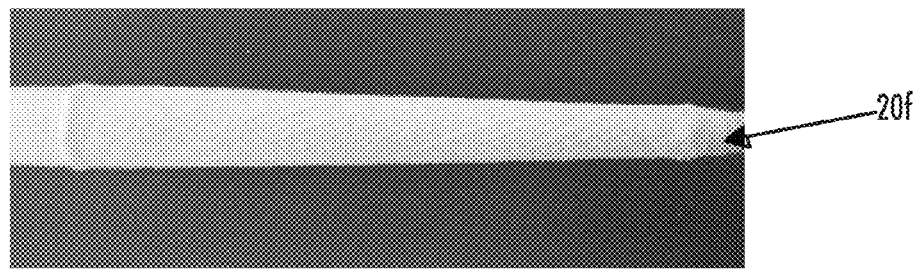
FIG. 20A is a digital photograph of a collagen construct comprising an inner collagen gel layer and an intermediate layer comprising at least one collagen fiber and gelatin/hydroxyapatite wrapped on a frustoconical support member according to embodiments of the present invention.
Figure 20B:
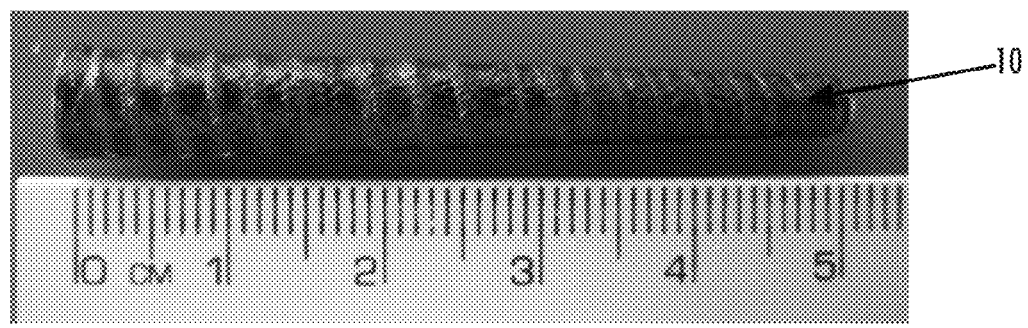
FIG. 20B is a digital photograph of a top view of a prototype of a tapered cross-linked collagen fiber construct with a rough outer surface according to embodiments of the present invention.

FIGS. 20A-B depict various stages in the formation of an exemplary tapered collagen fiber construct of the present invention. This exemplary embodiment may be particularly suitable for medical constructs. 500 mg of hydroxyapatite (677418-10G, HA nanopowder) can be mixed in 1 mL 2% Sigma gelatin A solution, to yield a gelatin/HA solution with a concentration of HA particles of 10% in gelatin.

Four layers of "pure" collagen gel (i.e., collagen gel with collagen, but no additional components or minerals) can be wrapped on a tapered Teflon® rod. Uncrosslinked collagen fibers can be wrapped on the collagen coated Teflon® rod, meanwhile a gelatin/HA solution can be painted along the fiber winding. FIG. 20A is a digital photograph of the collagen tube comprising the inner collagen gel layer and the intermediate layer comprising the collagen fiber painted with the gelatin/hydroxyapatite on a tapered rod. Two layers of collagen/HA gel (1% HA in neutralized collagen) can be wrapped on the fiber wound tube to make a rough surface. Then, four layers of 0.25% regular collagen gel can be wrapped on the HA coated tube. The tube can be crosslinked in 100 mL standard NDGA solution for approximately 24 hours, and then washed by phosphate buffer pH 10.3 and DI water, The tube can be air dried and taken off the rod. FIG. 20B depicts the completed exemplary tapered NDGA crosslinked collagen fiber construct (e.g,, tubes or sleeves).

Figure 20C:
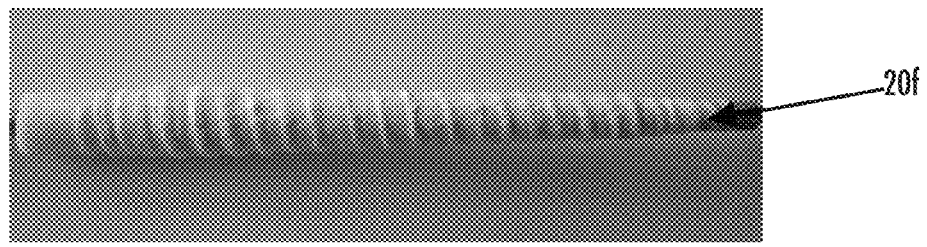
FIG. 20C is a digital photograph of a collagen fiber construct on a frustoconical support member according to embodiments of the present invention.
Figure 20D:
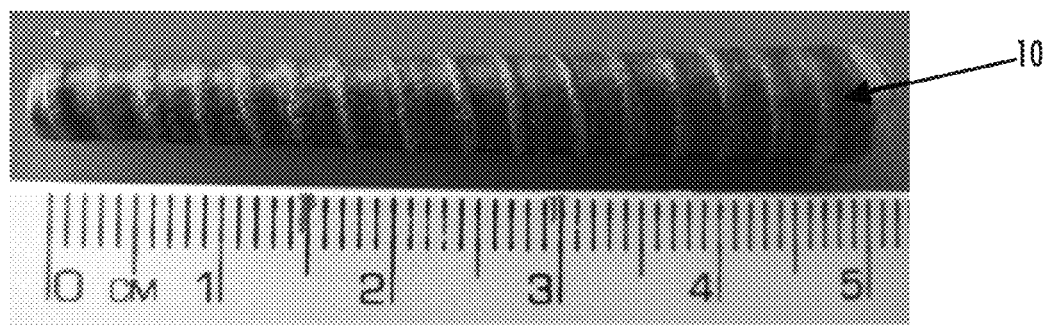
FIG. 20D is a digital photograph of a top view of a prototype of a tapered collagen fiber construct with a rough outer surface according to embodiments of the present invention.

FIGS. 20C-D depict various stages in the formation of an exemplary tapered collagen fiber construct of the present invention, which may be particularly suitable for medical constructs. This exemplary tapered collagen fiber construct (e.g., tube) can have an increased concentration of hydroxyapatite in the gelatin and collagen to provide a tube that is more rough and lighter in color. The collagen/HA can be prepared as follows 20 mL neutralized collagen+300 mg HA, final HA in collagen gel is 1.5%. Two layers of collagen/HA can be wrapped on the tube using approximately 10 mL of the collagen/HA gel. FIG. 20C is a digital photograph of the collagen fiber construct on the tapered rod with the collagen gel/hydroxyapatite layer applied. The gelatin/HA can be prepared as follows 5 mL 2.5% gelatin A+750 mg HA, final HA in gelatin solution is 15%. Approximately 2.5-3 mL of gelatin/HA can be painted on while winding the fibers. FIG. 20D depicts the completed exemplary tapered NDGA crosslinked collagen fiber construct (e.g., tubes or sleeves).

Figure 20E:
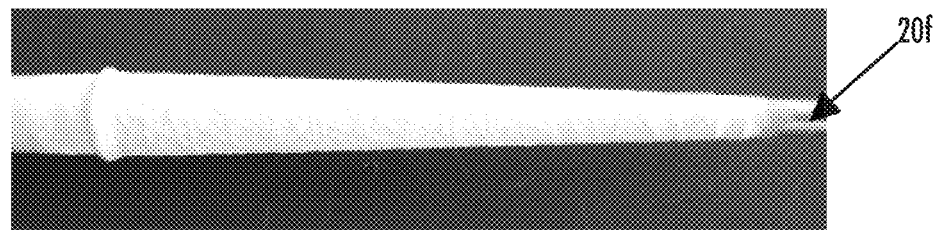
FIG. 20E is a digital photograph of a frustoconical support member wrapped with an inner collagen gel layer and an intermediate layer comprising at least one collagen fiber and gelatin/hydroxyapatite according to embodiments of the present invention.
Figure 20F:
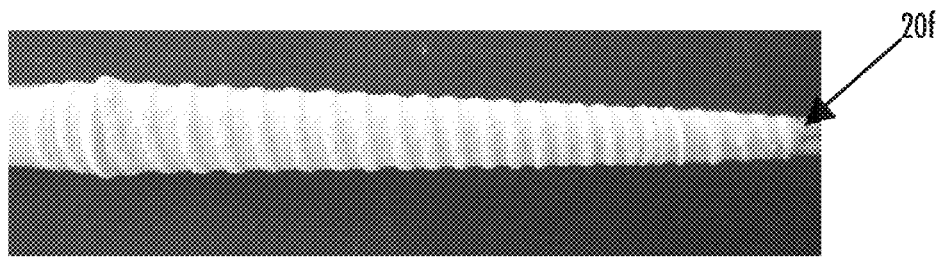
FIG. 20F is a digital photograph of the construct of FIG. 20E, further including a collagen gel/hydroxyapatite layer wrapped on the collagen fiber construct on the frustoconical support member according to embodiments of the present invention.
Figure 20G:
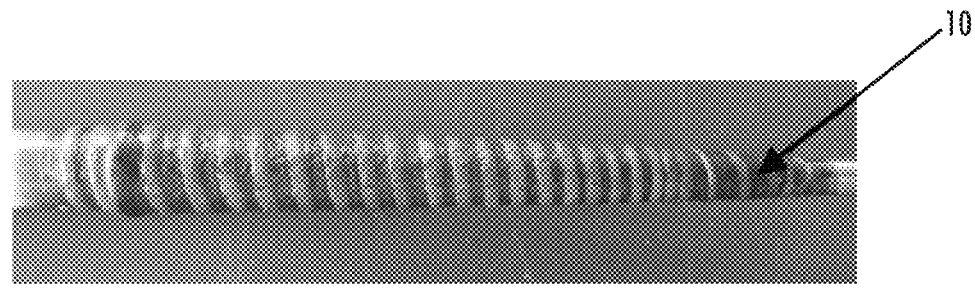
FIG. 20G is a digital photograph of a cross-linked collagen fiber construct with a rough outer surface on a frustoconical support member according to embodiments of the present invention.
Figure 20H:
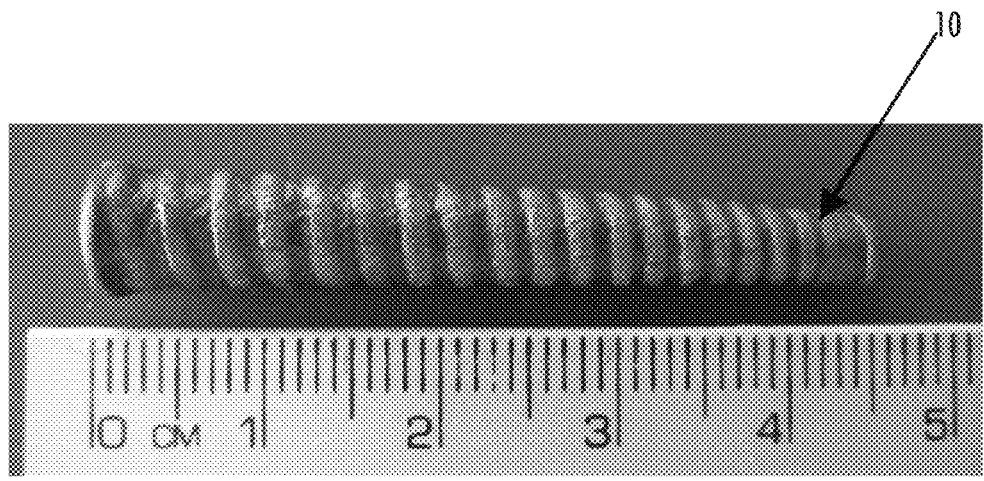
FIG. 20H is a digital photograph of a prototype of a tapered collagen fiber construct with a rough outer surface according to embodiments of the present invention.

FIGS. 20E-H depict various stages in the formation of an exemplary tapered collagen fiber construct of the present invention, which may be particularly suitable for medical constructs. This exemplary tapered collagen fiber construct (e.g., tube) can have more uniform stiffness from the end bigger in diameter to the end smaller in diameter along the longitudinal direction. Four layers of regular collagen gel can be wrapped on a tapered Teflon® rod. Uncrosslinked collagen fibers can be wound on the collagen coated Teflon® rod, meanwhile a gelatin/HA solution can be painted along the fiber winding. FIG. 20E is a digital photograph of the tapered rod wrapped with the collagen gel inner layer and the intermediate layer comprising the collagen fiber painted with gelatin/hydroxyapatite and is awaiting application of the rough surface. The concentration of HA particle can be 15% in 2.5% gelatin solution. One layer of collagen/HA gel (1.5% HA in neutralized collagen) can be wrapped on the fiber wound tube to make a rough surface. FIG. 20F is a digital photograph of the construct of FIG. 20E that has been wound with the collagen gel/hydroxyapatite layer. Three layers of 0.25% "pure" collagen gel can be wrapped on the HA coated tube. The tube can be crosslinked in 100 mL standard NDGA solution for approximately 24 hours, and then washed with phosphate buffer pH 10.3 and DI water. FIG. 20G is a digital photograph of the tapered NDGA cross-linked collagen fiber construct with a rough outer surface on the rod. The tube can be air dried. The tube can be sectioned and rehydrated, then taken off the rod. FIG. 20H depicts the completed exemplary tapered NDGA crosslinked collagen fiber construct (e.g., tubes or sleeves) with a rough outer surface.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of manufacturing a medical construct, comprising:
   providing at least one collagen fiber at a length of between about 1 m to about 100 m;
   winding the at least one collagen fiber a number of revolutions about a length of a support member having a long axis, the winding having at least one defined pitch and/or fiber angle relative to the long axis of the support member; and
   applying at least one layer of a gelatin slurry onto the at least one collagen fiber during the winding step to form a medical construct, wherein the gelatin slurry comprises one or more of the following minerals: calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and/or calcium sulfate.

2. A method according to claim 1, wherein the gelatin slurry has a gelatin concentration of between about 0.1% to about 40% weight per volume.

3. A method according to claim 1, wherein the at least one mineral comprises at least one of hydroxyapatite, tricalcium phosphate, and calcium sulfate.

4. A method according to claim 1, wherein the at least one mineral comprises hydroxyapatite.

5. A method according to claim 1, wherein the gelatin slurry has a mineral concentration of between about 0.1% to about 30% weight per volume.

6. A method according to claim 1, further comprising heating the gelatin slurry to a temperature of between about 45° C. and about 55° C. so that the gelatin slurry is in a liquid form during the applying step.

7. A method according to claim 1, further comprising placing a gel of soluble collagen having a substantially cylindrical shape on the support member before the winding step, then placing a gel of soluble collagen over the at least one collagen fiber during and/or after the winding step.

8. A method according to claim 1, further comprising placing a gel of soluble collagen comprising one or more minerals on the support member before the winding step to form a rough inner surface of the construct.

9. A method according to claim 8, wherein the one or more minerals is selected from the following minerals: calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and/or calcium sulfate.

10. A method according to claim 1, further comprising placing a gel of soluble collagen comprising one or more minerals over the at least one collagen fiber after the applying step to form a rough outer surface of the construct.

11. A method according to claim 10, wherein the one or more minerals is selected from the following minerals: calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and/or calcium sulfate.

12. A method according to claim 1, wherein the support member is substantially cylindrical or frustoconical.

13. A method according to claim 1, wherein the support member is substantially rectangular.

14. A method according to claim 1, wherein the support member comprises ribs, and the method comprises forming a ribbed pattern on the construct based on direct or indirect contact of the at least one collagen fiber with the ribs.

15. A method according to claim 1, further comprising allowing the collagen fiber with the gelatin slurry to dry to a low moisture content state to provide a gelatin film, then polymerizing the at least partially dried collagen fiber with the gelatin film using a cross-linking agent selected from the group consisting of: NDGA, carbodiimide, glutaraldehyde, formaldehyde, tannic acid, isocyanates, and epoxy resins.

16. A method according to claim 1, further comprising allowing the collagen fiber with the gelatin slurry to dry to a low moisture content state to provide a gelatin film, then polymerizing the at least partially dried collagen fiber with the gelatin film using NDGA cross-linking.

17. A method according to claim 1, wherein the at least one collagen fiber includes at least one collagen fiber bundle.

18. A method according to claim 1, wherein the winding step is carried out to form multiple overlying layers of the at least one collagen fiber in one or more fiber angles so that the at least one fiber intersects itself at different locations along a length of the construct.

19. A method according to claim 1, wherein the construct is an allo-graft and/or auto-graft for tendon or ligament implants.

20. A method according to claim 1, further comprising placing a gel of soluble collagen comprising one or more minerals on the support member before the winding step to form a rough inner surface of the construct and placing a gel of soluble collagen comprising one or more minerals over the at least one collagen fiber after the applying step to form a rough outer surface of the construct,
   wherein the one or more minerals in the gel of soluble collagen forming the rough inner surface of the construct and the gel of soluble collagen forming the rough outer surface of the construct are present in a different concentration than the concentration of the one or more minerals in the gelatin slurry.

21. A method according to claim 20, wherein the gel of soluble collagen forming the rough inner surface of the construct, the gel of soluble collagen forming the rough outer surface of the construct, and the gelatin slurry each comprise at least one different mineral.

22. A method of manufacturing a medical construct, comprising:
   placing a soluble collagen gel having a substantially cylindrical shape on an outer surface of a support member;
   drying the soluble collagen gel to a low moisture content state to form an inner layer of collagen film on the support member; then
   winding at least one collagen fiber about the support member over the collagen film;
   applying a gelatin slurry comprising at least one mineral to a surface of the at least one collagen fiber on the support member;
   drying the wound collagen fiber with the gelatin slurry to a low moisture content state to form a gelatin film; then
   placing a soluble collagen gel over the at least partially dried collagen fiber with the gelatin film; and
   drying the applied collagen gel to form an outer layer of collagen film.

23. A method according to claim 22, wherein the at least one mineral is selected from the following minerals: calcium phosphate, calcium hydrogen phosphate, calcium dihydrogen phosphate, monotite, brushite, calcium pyrophosphate, tricalcium phosphate, tetracalcium phosphate, octacalcium phosphate, amorphous calcium phosphate, hydroxyapatite, carbonateapatite, calcite, and/or calcium sulfate.

24. A method according to claim 22, wherein the at least one mineral comprises at least one of hydroxyapatite, tricalcium phosphate, and calcium sulfate.

25. A method according to claim 22, wherein the at least one mineral comprises hydroxyapatite.

26. A method according to claim 22, further comprising heating the gelatin slurry to a temperature of between about 45° C. and about 55° C. so that the gelatin slurry is in a liquid form during the applying step.

27. A method according to claim 22, wherein each of the placing steps are carried out to place multiple layers of the collagen gel.

28. A method according to claim 27, wherein the multiple layers of collagen gel comprise different components and/or different concentrations of components, and wherein the components are selected from the group consisting of collagen and minerals.

29. A method according to claim 27, wherein between about 1 to about 10 layers of the collagen gel comprise at least one mineral.

30. A method according to claim 22, wherein the at least one collagen fiber includes at least one collagen fiber bundle.

31. A method according to claim 22, further comprising polymerizing the collagen fiber construct while the construct is held on the support member using a cross-linking agent selected from the group consisting of: NDGA, carbodiimide, glutaraldehyde, formaldehyde, tannic acid, isocyanates, and epoxy resins, then removing the support member.

32. A method according to claim 22, further comprising polymerizing the collagen fiber construct while the construct is held on the support member using NDGA cross-linking, then removing the support member.

33. A method according to claim 22, wherein the winding step is carried out to form multiple overlying layers of the at least one collagen fiber in one or more fiber angles so that the at least one fiber intersects itself at different locations along a length of the construct.

34. A method according to claim 22, wherein the applying step is carried out by applying the gelatin slurry onto the at least one collagen fiber during the winding step.

35. A method according to claim 22, wherein the inner layer of collagen film and/or the outer layer of collagen film comprise one or more minerals, and the one or more minerals in the inner layer of collagen film and/or the outer layer of collagen film are present in a different concentration than the concentration of the at least one mineral in the gelatin slurry.

36. A method according to claim 35, wherein the at least one mineral in the gelatin slurry is different than the one or more minerals in the inner layer of collagen film and/or the outer layer of collagen film.

* * * * *

UNITED STATES PATENT AND TRADEMARK OFFICE
CERTIFICATE OF CORRECTION

| | | |
|---|---|---|
| PATENT NO. | : 9,179,976 B2 | Page 1 of 1 |
| APPLICATION NO. | : 13/153665 | |
| DATED | : November 10, 2015 | |
| INVENTOR(S) | : Paulos et al. | |

It is certified that error appears in the above-identified patent and that said Letters Patent is hereby corrected as shown below:

On Title Page:
Item (56) References Cited, OTHER PUBLICATIONS, Page 2, Line 52:
Please correct "product=198," to read -- product=88, --

In the Specification:
Column 5, Line 57: Please correct "invention," to read -- invention. --
Column 18, Line 25: Please correct "$13_1...13_n$," to read -- $13_1$- $13n$ --
Column 27, Line 11: Please correct "(pH 72)" to read -- (pH 7.2) --

In the Claims:
Column 29, Claim 1, Lines 13 and 14:
Please correct "a medical construct, wherein the gelatin slurry comprises one or more of the following minerals:"
  to read as
  -- a medical construct,
wherein the gelatin slurry comprises one or more of the following minerals: --

Signed and Sealed this
Ninth Day of August, 2016

Michelle K. Lee
*Director of the United States Patent and Trademark Office*